(12) United States Patent
Beer

(10) Patent No.: US 10,520,403 B2
(45) Date of Patent: Dec. 31, 2019

(54) APPARATUSES FOR HEATING MICROSCOPE SLIDES CARRYING SPECIMENS

(71) Applicant: Ventana Medical Systems, Inc., Tucson, AZ (US)

(72) Inventor: Jonathan Peter Beer, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 16/102,598

(22) Filed: Aug. 13, 2018

(65) Prior Publication Data
US 2018/0348100 A1    Dec. 6, 2018

Related U.S. Application Data

(63) Continuation of application No. 16/010,357, filed on Jun. 15, 2018, now Pat. No. 10,429,280, which is a
(Continued)

(51) Int. Cl.
*G01N 1/00*    (2006.01)
*G01N 1/30*    (2006.01)
(Continued)

(52) U.S. Cl.
CPC .............. *G01N 1/30* (2013.01); *G01N 1/312* (2013.01); *G01N 35/00029* (2013.01);
(Continued)

(58) Field of Classification Search
CPC .... G01N 1/30; G01N 1/312; G01N 35/00029; G01N 35/0099; G01N 2035/00138; G01N 2035/00346; H05B 1/02
(Continued)

(56) References Cited

U.S. PATENT DOCUMENTS 3,219,416 A    11/1965  Natelson
3,574,064 A     4/1971  Binnings et al.
(Continued)

FOREIGN PATENT DOCUMENTS

AU    2005203557    8/2006
AU    2003224987    9/2009
(Continued)

OTHER PUBLICATIONS

"Coverslips and Stainers," Hacker Instruments and Industries, Inc., 3 pages, [retrieved on Apr. 18, 2001]. Retrieved from the Internet <URL:http://hackerinstruments.com/coverslippers.htm>.
(Continued)

*Primary Examiner* — Mark H Paschall
(74) *Attorney, Agent, or Firm* — Perkins Coie LLP

(57) ABSTRACT

A slide processing apparatus controls the temperature and orientation of a microscope slide carrying one or more specimens. The apparatus heats the specimen-bearing microscope slide while the slide is oriented to both facilitate adhesion between the specimens and the slide and control movement of the specimens relative to the microscope slide. A slide dryer of the apparatus conductively heats the specimens using a conductive slide heater that physically engages the microscope slide.

20 Claims, 10 Drawing Sheets

Related U.S. Application Data continuation of application No. 13/128,856, filed as application No. PCT/US2009/064235 on Nov. 12, 2009, now Pat. No. 10,184,862.

(60) Provisional application No. 61/113,964, filed on Nov. 12, 2008.

(51) Int. Cl.
  *G01N 1/31* (2006.01)
  *G01N 35/00* (2006.01)
  *H05B 1/02* (2006.01)

(52) U.S. Cl.
  CPC ............... *G01N 35/0099* (2013.01); *G01N 2035/00138* (2013.01); *G01N 2035/00168* (2013.01); *G01N 2035/00346* (2013.01)

(58) Field of Classification Search
  USPC ........ 435/404–406; 219/494, 385, 486, 506; 392/382
  See application file for complete search history.

(56) References Cited

U.S. PATENT DOCUMENTS

| | | |
|---|---|---|
| 3,650,437 A | 3/1972 | Binnings et al. |
| 3,665,148 A | 5/1972 | Yasenchak et al. |
| 3,695,281 A | 10/1972 | Leon |
| 3,853,092 A | 12/1974 | Amos et al. |
| 3,854,703 A | 12/1974 | Gibbs et al. |
| 3,979,576 A | 9/1976 | Janson |
| 4,013,038 A | 3/1977 | Rogers et al. |
| 4,043,292 A * | 8/1977 | Rogers ............... G01N 1/312 118/319 |
| 4,058,367 A | 11/1977 | Gilford |
| 4,092,952 A | 6/1978 | Wilkie et al. |
| 4,245,967 A | 1/1981 | Busselet |
| RE30,730 E | 9/1981 | Duff |
| 4,286,637 A | 9/1981 | Wilson |
| 4,298,571 A | 11/1981 | DiFulvio et al. |
| 4,346,056 A | 8/1982 | Sakurada |
| 4,358,470 A | 11/1982 | Rasmussen |
| 4,384,193 A | 5/1983 | Kledzik et al. |
| 4,406,547 A | 9/1983 | Aihara |
| 4,430,299 A | 2/1984 | Horne |
| 4,447,395 A | 5/1984 | Englar et al. |
| 4,453,807 A | 6/1984 | Faulkner et al. |
| 4,455,280 A | 6/1984 | Shinohara et al. |
| 4,484,293 A | 11/1984 | Minucciani et al. |
| 4,528,159 A | 7/1985 | Liston |
| 4,539,855 A | 9/1985 | Jacobs |
| 4,543,236 A | 9/1985 | Von Gise |
| 4,577,514 A | 3/1986 | Bradley et al. |
| 4,584,275 A | 4/1986 | Okano et al. |
| 4,629,862 A | 12/1986 | Kitagawa et al. |
| 4,643,879 A | 2/1987 | Hanaway |
| 4,647,431 A | 3/1987 | Sekine et al. |
| 4,648,023 A | 3/1987 | Powell |
| 4,659,971 A | 4/1987 | Suzuki et al. |
| 4,670,974 A | 6/1987 | Antoszewski et al. |
| 4,676,951 A | 6/1987 | Armes et al. |
| 4,678,752 A | 7/1987 | Thorne et al. |
| 4,681,741 A | 7/1987 | Hanaway |
| 4,695,430 A | 9/1987 | Coville et al. |
| 4,708,886 A | 11/1987 | Nelson |
| 4,720,463 A | 1/1988 | Farber et al. |
| 4,727,409 A | 2/1988 | Conner et al. |
| 4,727,494 A | 2/1988 | Buote |
| 4,729,661 A | 3/1988 | Bell |
| 4,731,335 A | 3/1988 | Brigati |
| 4,738,824 A | 4/1988 | Takeuchi |
| 4,764,342 A | 8/1988 | Kelln et al. |
| 4,774,055 A | 9/1988 | Iwasaki et al. |
| 4,777,020 A | 10/1988 | Brigati |
| 4,781,891 A | 11/1988 | Galle et al. |
| 4,795,710 A | 1/1989 | Muszak et al. |
| 4,798,706 A | 1/1989 | Brigati |
| 4,801,431 A | 1/1989 | Cuomo et al. |
| 4,805,469 A | 2/1989 | Commarmot |
| 4,807,152 A | 2/1989 | Lane et al. |
| 4,815,978 A | 3/1989 | Mazza et al. |
| 4,835,711 A | 5/1989 | Hutchins et al. |
| 4,837,159 A | 6/1989 | Yamada |
| 4,843,566 A | 6/1989 | Gordon et al. |
| 4,844,868 A | 7/1989 | Rokugawa |
| 4,847,208 A | 7/1989 | Bogen |
| 4,852,001 A | 7/1989 | Tsushima et al. |
| 4,855,109 A | 8/1989 | Muraishi et al. |
| 4,857,272 A | 8/1989 | Sugaya |
| 4,858,155 A | 8/1989 | Okawa et al. |
| 4,865,986 A | 9/1989 | Coy et al. |
| 4,895,706 A | 1/1990 | Root et al. |
| 4,896,269 A | 1/1990 | Tong |
| 4,902,481 A | 2/1990 | Clark et al. |
| 4,911,098 A | 3/1990 | Tabata |
| 4,911,915 A | 3/1990 | Fredenburgh |
| 4,919,887 A | 4/1990 | Wakatake |
| 4,928,540 A | 5/1990 | Kido et al. |
| 4,933,146 A | 6/1990 | Meyer et al. |
| 4,935,875 A | 6/1990 | Shah et al. |
| 4,961,906 A | 10/1990 | Andersen et al. |
| 4,964,544 A | 10/1990 | Hanna et al. |
| 4,965,049 A | 10/1990 | Lillig et al. |
| 4,971,913 A | 11/1990 | Manabe et al. |
| 4,975,250 A | 12/1990 | Mordecki |
| 4,979,093 A | 12/1990 | Laine et al. |
| 4,979,128 A | 12/1990 | Seki et al. |
| 4,985,206 A | 1/1991 | Bowman et al. |
| 5,002,736 A | 3/1991 | Babbitt et al. |
| 5,023,187 A | 6/1991 | Koebler et al. |
| 5,030,418 A | 7/1991 | Miyata |
| 5,035,866 A | 7/1991 | Wannlund |
| 5,040,123 A | 8/1991 | Barber et al. |
| 5,051,238 A | 9/1991 | Umetsu et al. |
| 5,073,504 A | 12/1991 | Bogen |
| 5,075,079 A | 12/1991 | Kerr et al. |
| 5,089,229 A | 2/1992 | Heidt et al. |
| 5,093,557 A | 3/1992 | Lok et al. |
| 5,096,670 A | 3/1992 | Harris et al. |
| 5,104,621 A | 4/1992 | Pfost et al. |
| 5,105,066 A | 4/1992 | Houdy et al. |
| 5,116,496 A | 5/1992 | Scott |
| 5,122,342 A | 6/1992 | McCulloch et al. |
| 5,122,959 A | 6/1992 | Nathanson et al. |
| 5,148,370 A | 9/1992 | Litt et al. |
| 5,154,889 A | 10/1992 | Muraishi |
| 5,168,453 A | 12/1992 | Nomaru et al. |
| 5,180,606 A | 1/1993 | Stokes et al. |
| 5,181,259 A | 1/1993 | Rorvig |
| 5,207,987 A | 5/1993 | Kureshy et al. |
| 5,209,903 A | 5/1993 | Kanamori et al. |
| 5,218,645 A | 6/1993 | Bacus |
| 5,229,074 A | 7/1993 | Heath et al. |
| 5,231,029 A | 7/1993 | Wootton et al. |
| 5,232,655 A | 8/1993 | Burkovich et al. |
| 5,232,664 A | 8/1993 | Krawzak et al. |
| 5,233,533 A | 8/1993 | Edstrom et al. |
| 5,246,665 A | 9/1993 | Tyranski et al. |
| 5,266,272 A | 11/1993 | Griner et al. |
| 5,273,905 A | 12/1993 | Muller et al. |
| 5,280,156 A | 1/1994 | Niori et al. |
| 5,282,149 A | 1/1994 | Grandone et al. |
| 5,304,347 A | 4/1994 | Mann et al. |
| 5,311,426 A | 5/1994 | Donohue et al. |
| 5,314,825 A | 5/1994 | Weyrauch et al. |
| 5,316,452 A | 5/1994 | Bogen et al. |
| 5,316,726 A | 5/1994 | Babson et al. |
| 5,332,549 A | 7/1994 | MacIndoe, Jr. |
| 5,334,353 A | 8/1994 | Blattner |
| 5,352,612 A | 10/1994 | Huber et al. |
| 5,355,439 A | 10/1994 | Bernstein et al. |
| 5,355,695 A | 10/1994 | Kawaguchi |
| 5,356,595 A | 10/1994 | Kanamori et al. |

(56) References Cited

U.S. PATENT DOCUMENTS

| | | |
|---|---|---|
| 5,356,814 A | 10/1994 | Carrico, Jr. et al. |
| 5,358,691 A | 10/1994 | Clark et al. |
| 5,376,313 A | 12/1994 | Kanewske, III et al. |
| 5,402,350 A | 3/1995 | Kline |
| 5,424,036 A | 6/1995 | Ushikubo |
| 5,425,918 A | 6/1995 | Healey et al. |
| 5,428,470 A | 6/1995 | Labriola, II |
| 5,431,309 A | 7/1995 | Ophardt |
| 5,439,645 A | 8/1995 | Saralegui et al. |
| 5,439,649 A | 8/1995 | Tseung et al. |
| 5,446,652 A | 8/1995 | Peterson et al. |
| 5,475,610 A | 12/1995 | Atwood et al. |
| 5,479,581 A | 12/1995 | Kleinschnitz |
| 5,496,518 A | 3/1996 | Arai et al. |
| 5,512,248 A | 4/1996 | Van |
| 5,523,056 A | 6/1996 | Miller |
| 5,525,302 A | 6/1996 | Astte |
| 5,525,515 A | 6/1996 | Blattner |
| 5,573,727 A | 11/1996 | Keefe |
| 5,575,976 A | 11/1996 | Choperena et al. |
| 5,576,215 A | 11/1996 | Burns et al. |
| 5,578,455 A | 11/1996 | Tosa et al. |
| 5,595,707 A | 1/1997 | Copeland et al. |
| 5,601,141 A | 2/1997 | Gordon et al. |
| 5,614,376 A | 3/1997 | Copley et al. |
| 5,629,201 A | 5/1997 | Nugteren et al. |
| 5,639,665 A | 6/1997 | Arai et al. |
| 5,645,114 A | 7/1997 | Bogen et al. |
| 5,645,800 A | 7/1997 | Masterson et al. |
| 5,646,046 A | 7/1997 | Fischer et al. |
| 5,646,049 A | 7/1997 | Tayi |
| 5,650,327 A | 7/1997 | Copeland et al. |
| 5,654,199 A | 8/1997 | Copeland et al. |
| 5,654,200 A | 8/1997 | Copeland et al. |
| 5,656,493 A | 8/1997 | Mullis et al. |
| 5,672,512 A | 9/1997 | Shaw |
| 5,674,454 A | 10/1997 | Karl et al. |
| 5,675,700 A * | 10/1997 | Atwood ............... B01J 19/0046 219/521 |
| 5,675,715 A | 10/1997 | Bernstein et al. |
| 5,690,892 A | 11/1997 | Babler et al. |
| 5,695,718 A | 12/1997 | Imai et al. |
| 5,696,887 A | 12/1997 | Bernstein |
| 5,700,346 A | 12/1997 | Edwards |
| 5,736,105 A | 4/1998 | Astle |
| 5,737,498 A | 4/1998 | Murray |
| 5,737,499 A | 4/1998 | Bernstein et al. |
| 5,819,842 A | 10/1998 | Potter et al. |
| 5,839,091 A | 11/1998 | Rhett et al. |
| 5,854,075 A | 12/1998 | Levine et al. |
| 5,861,094 A | 1/1999 | Goehde |
| 5,869,006 A | 2/1999 | Fanning et al. |
| 5,871,696 A | 2/1999 | Roberts et al. |
| 5,875,286 A | 2/1999 | Bernstein et al. |
| 5,895,628 A | 4/1999 | Heid et al. |
| 5,909,674 A | 6/1999 | Schaffer et al. |
| 5,917,675 A | 6/1999 | Yang |
| 5,930,461 A | 7/1999 | Bernstein et al. |
| 5,947,167 A | 9/1999 | Bogen et al. |
| 5,948,349 A | 9/1999 | Beurotte et al. |
| 5,948,359 A | 9/1999 | Kalra et al. |
| 5,958,341 A | 9/1999 | Chu |
| 5,975,740 A | 11/1999 | Lin et al. |
| 5,985,669 A | 11/1999 | Palander |
| 5,985,672 A | 11/1999 | Kegelman et al. |
| 6,004,512 A | 12/1999 | Titcomb et al. |
| 6,017,495 A | 1/2000 | Ljungmann |
| 6,096,271 A | 3/2000 | Bogen et al. |
| 6,054,099 A | 4/2000 | Levy |
| 6,068,393 A | 5/2000 | Hutchins et al. |
| 6,076,583 A | 6/2000 | Edwards |
| 6,080,363 A | 6/2000 | Takahashi et al. |
| 6,093,574 A | 7/2000 | Druyor-Sanchez et al. |
| 6,110,425 A | 8/2000 | Gao et al. |
| 6,133,548 A | 10/2000 | Grover et al. |
| 6,136,270 A | 10/2000 | Maes et al. |
| 6,143,512 A | 11/2000 | Markovic et al. |
| 6,180,060 B1 | 1/2001 | Green et al. |
| 6,180,061 B1 | 1/2001 | Bogen et al. |
| 6,183,645 B1 | 2/2001 | DeWitt |
| 6,183,693 B1 | 2/2001 | Bogen et al. |
| 6,193,933 B1 | 2/2001 | Sasaki et al. |
| 6,258,322 B1 | 7/2001 | Meikle |
| 6,284,543 B1 | 9/2001 | Alvarez |
| 6,296,764 B1 | 10/2001 | Guirguis et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,358,473 B1 | 3/2002 | Coello et al. |
| 6,368,067 B1 | 4/2002 | Stutz |
| 6,372,144 B1 | 4/2002 | Vassarotti |
| 6,387,326 B1 | 5/2002 | Edwards et al. |
| 6,395,554 B1 | 5/2002 | Regan et al. |
| 6,403,931 B1 * | 6/2002 | Showalter ............... B01L 7/00 219/483 |
| 6,436,348 B1 | 8/2002 | Ljungmann et al. |
| 6,451,551 B1 | 9/2002 | Zhan et al. |
| 6,471,958 B2 | 10/2002 | Dimitrijevich et al. |
| 6,472,217 B1 | 10/2002 | Richards et al. |
| 6,495,106 B1 | 12/2002 | Kalra et al. |
| 6,512,209 B1 | 1/2003 | Yano |
| 6,537,818 B2 | 3/2003 | Richards et al. |
| 6,544,798 B1 | 4/2003 | Christensen et al. |
| 6,585,936 B1 | 7/2003 | Shah |
| 6,594,537 B1 | 7/2003 | Bernstein et al. |
| 6,605,475 B1 | 8/2003 | Taylor et al. |
| 6,626,224 B1 | 9/2003 | Ljungmann |
| 6,632,598 B1 | 10/2003 | Zhang et al. |
| 6,635,225 B1 | 10/2003 | Thiem et al. |
| 6,649,128 B1 | 11/2003 | Meyer et al. |
| 6,685,884 B2 | 2/2004 | Styili et al. |
| 6,703,247 B1 | 3/2004 | Chu |
| 6,746,851 B1 | 6/2004 | Tseung et al. |
| 6,759,011 B1 | 7/2004 | Richards et al. |
| 6,821,072 B2 | 11/2004 | Thiem et al. |
| 6,827,900 B2 | 12/2004 | Thiem et al. |
| 6,827,901 B2 | 12/2004 | Copeland et al. |
| 6,855,559 B1 | 2/2005 | Christensen et al. |
| 6,881,579 B2 | 4/2005 | Hilson et al. |
| 6,887,428 B2 | 5/2005 | Wernz et al. |
| 6,979,425 B1 | 12/2005 | Ganz et al. |
| 6,998,094 B2 | 2/2006 | Haslam et al. |
| 6,998,270 B2 | 2/2006 | Tseung et al. |
| 7,153,474 B2 | 12/2006 | Thiem |
| 7,262,022 B2 | 8/2007 | Chu |
| 7,270,785 B1 | 9/2007 | Lemme et al. |
| 7,271,006 B2 | 9/2007 | Reinhardt et al. |
| 7,273,591 B2 | 9/2007 | Sellers et al. |
| 7,303,725 B2 * | 12/2007 | Reinhardt ............... B01L 9/52 422/63 |
| 7,314,595 B2 | 1/2008 | Honkanen et al. |
| 7,368,081 B2 | 5/2008 | Thiem |
| 7,396,508 B1 | 7/2008 | Richards et al. |
| 7,400,983 B2 * | 7/2008 | Feingold ............... G01N 1/30 702/31 |
| 7,435,383 B2 | 10/2008 | Tseung et al. |
| 7,468,161 B2 | 12/2008 | Reinhardt et al. |
| 7,501,283 B2 | 3/2009 | Hersch et al. |
| 7,553,672 B2 | 6/2009 | Bogen et al. |
| 7,584,019 B2 | 9/2009 | Feingold et al. |
| 7,744,817 B2 | 6/2010 | Bui |
| 7,860,727 B2 | 12/2010 | Showalter et al. |
| 8,048,373 B2 | 11/2011 | Reinhardt et al. |
| 8,501,434 B2 | 8/2013 | Barker et al. |
| 8,663,991 B2 | 3/2014 | Reinhardt et al. |
| 8,719,053 B2 | 5/2014 | Showalter et al. |
| 8,765,476 B2 | 7/2014 | Avantsa et al. |
| 2001/0004449 A1 | 6/2001 | Suzuki et al. |
| 2001/0016358 A1 | 8/2001 | Osawa et al. |
| 2001/0019702 A1 | 9/2001 | Watari et al. |
| 2001/0019703 A1 | 9/2001 | Thiem et al. |
| 2001/0055545 A1 | 12/2001 | Takii et al. |
| 2002/0018733 A1 | 2/2002 | Kapplein et al. |
| 2002/0037239 A1 | 3/2002 | Komatsu |

(56) References Cited

U.S. PATENT DOCUMENTS

| | | |
|---|---|---|
| 2002/0054830 A1 | 5/2002 | Bogen et al. |
| 2002/0057992 A1 | 5/2002 | Eckert et al. |
| 2002/0064482 A1 | 5/2002 | Tisone et al. |
| 2002/0110494 A1 | 8/2002 | Lemme et al. |
| 2002/0116132 A1 | 8/2002 | Rhett et al. |
| 2003/0026732 A1 | 2/2003 | Gordon et al. |
| 2003/0047863 A1 | 3/2003 | Lang et al. |
| 2003/0049104 A1 | 3/2003 | Thiem et al. |
| 2003/0092186 A1 | 5/2003 | Pressman et al. |
| 2003/0099580 A1 | 5/2003 | Pressman et al. |
| 2003/0161761 A1 | 8/2003 | Williams et al. |
| 2003/0203493 A1 | 10/2003 | Lemme et al. |
| 2003/0211630 A1 | 11/2003 | Richards et al. |
| 2003/0215357 A1 | 11/2003 | Malterer et al. |
| 2003/0215936 A1 | 11/2003 | Kallioniemi et al. |
| 2004/0002163 A1 | 1/2004 | Reinhardt et al. |
| 2004/0009098 A1 | 1/2004 | Torre-Bueno |
| 2004/0038408 A1 | 2/2004 | Abbott et al. |
| 2004/0052685 A1 | 3/2004 | Richards et al. |
| 2004/0092024 A1 | 5/2004 | Reinhardt et al. |
| 2004/0121485 A1 | 6/2004 | Hopkins et al. |
| 2004/0136868 A1 | 7/2004 | Bevirt et al. |
| 2004/0197230 A1 | 10/2004 | Lemme et al. |
| 2005/0042137 A1 | 2/2005 | Petersen et al. |
| 2005/0047971 A1 | 3/2005 | Clements et al. |
| 2005/0053526 A1 | 3/2005 | Angros |
| 2005/0089444 A1 | 4/2005 | Justin et al. |
| 2005/0118670 A1 | 6/2005 | Lihl et al. |
| 2005/0186114 A1 | 8/2005 | Reinhardt et al. |
| 2005/0238534 A1 | 10/2005 | Chu |
| 2005/0250211 A1 | 11/2005 | Reinhardt et al. |
| 2006/0088928 A1 | 4/2006 | Sweet et al. |
| 2006/0120621 A1 | 6/2006 | Larkin et al. |
| 2006/0120921 A1 | 6/2006 | Elliot et al. |
| 2006/0120925 A1 | 6/2006 | Takayama et al. |
| 2006/0127276 A1 | 6/2006 | Ljungmann et al. |
| 2006/0134732 A1 | 6/2006 | Kram et al. |
| 2007/0128073 A1* | 6/2007 | Tappen ............... G01N 1/2813 422/65 |
| 2011/0215081 A1 | 9/2011 | Beer |
| 2014/0178858 A1 | 6/2014 | Reinhardt et al. |

FOREIGN PATENT DOCUMENTS

| | | |
|---|---|---|
| CA | 2321823 | 9/1999 |
| CA | 2482441 | 10/2003 |
| EP | 240134 | 10/1987 |
| EP | 508568 | 10/1992 |
| EP | 611598 | 8/1994 |
| EP | 517835 | 2/1996 |
| EP | 722363 | 4/1999 |
| EP | 600939 | 10/1999 |
| EP | 1052497 | 11/2000 |
| EP | 1477838 | 11/2004 |
| EP | 1890127 | 2/2008 |
| FR | 2239167 | 2/1975 |
| FR | 2528122 | 12/1983 |
| GB | 2143205 | 2/1985 |
| GB | 2216259 | 10/1989 |
| JP | 55-014157 | 1/1980 |
| JP | 55-107957 | 8/1980 |
| JP | 61-219847 | 9/1986 |
| JP | 63-203761 | 8/1988 |
| JP | 04-356845 | 12/1992 |
| JP | 05-87817 | 4/1993 |
| JP | 05-087817 | 4/1993 |
| JP | 05-504627 | 7/1993 |
| JP | 06-245771 | 9/1994 |
| JP | 09-503304 | 3/1997 |
| JP | 09-196565 | 7/1997 |
| JP | 10-104136 | 4/1998 |
| JP | 11-083703 | 3/1999 |
| JP | 11-83703 | 3/1999 |
| JP | 11-502926 | 9/1999 |
| JP | 2001-242175 | 9/2001 |
| JP | 2001-516869 | 10/2001 |
| JP | 2002-511600 | 4/2002 |
| JP | 2002-267642 | 9/2002 |
| JP | 2002-267942 | 9/2002 |
| JP | 2003-344242 | 12/2003 |
| JP | 2004-506228 | 2/2004 |
| JP | 2005-527811 | 9/2005 |
| JP | 2013-092532 | 5/2013 |
| WO | 1987000086 | 1/1987 |
| WO | 1988002865 | 4/1988 |
| WO | 1991013335 | 9/1991 |
| WO | 1992001919 | 2/1992 |
| WO | 1992019952 | 11/1992 |
| WO | 1993023732 | 11/1993 |
| WO | 1995010035 | 4/1995 |
| WO | 1995024498 | 9/1995 |
| WO | 1999009390 | 2/1999 |
| WO | 1999044032 | 9/1999 |
| WO | 1999053357 | 10/1999 |
| WO | 2000014534 | 3/2000 |
| WO | 2000062035 | 10/2000 |
| WO | 2001051909 | 7/2001 |
| WO | 2001073399 | 10/2001 |
| WO | 2002012857 | 2/2002 |
| WO | 2002074525 | 9/2002 |
| WO | 2003045560 | 6/2003 |
| WO | 2003052386 | 6/2003 |
| WO | 2003089140 | 10/2003 |
| WO | 2003091710 | 11/2003 |
| WO | 2003106157 | 12/2003 |
| WO | 2004001390 | 12/2003 |
| WO | 2004008106 | 1/2004 |
| WO | 2004074845 | 9/2004 |
| WO | 2005031312 | 4/2005 |
| WO | 2006073910 | 7/2006 |

OTHER PUBLICATIONS

"Advanta CV/AS," Article from Vision Instruments, Date: Unknown (for purposes of examination date is assumed to be prior to filing date of Apr. 15, 2002), 2 pgs.

"DAKO Autostainer Features and Specifications," DAKO Corporation, 3 pages, [retrieved on Dec. 7, 2000]. Retrieved from the Internet <URL: http://www.dakousa.com>.

"i 6000," Article from BioGenex, 2000, 4 pages.

"Laboratory Equipment 1998 and 1999," article from Shandon, Inc., pp. 37-51.

"Leica Auto Stainer XL," Article from Leica, Date: Unknown (for purposes of examination date is assumed to be prior to filing date of Apr. 15, 2002), 4 pgs.

"Robot-Stainer HMS 760, Automatic Slide Stainer for Routine Histology and Cytology Applications," Article from Microm Histology Products, Date: Unknown (for purposes of examination date is assumed to be prior to filing date of Apr. 15, 2002), 4 pgs.

"Sakura Tissue-Tek DRS 2000 Slide Stainer," article from Sakura Finetek U.S.A., Inc., 1998, 1 page.

"ST 5050 Zymed's Sensible IHC Automated Staining Solution," Article from Zymed Laboratories, Date: Unknown (for purposes of examination date is assumed to be prior to filing date of Apr. 15, 2002), 2 pgs.

"The New Protocol in Staining Technology," Article from Fisher Healthcare, Date: Unknown (for purposes of examination date is assumed to be prior to filing date of Apr. 15, 2002), 5 pgs.

"Tissue-Stainer TST 40," Article from Medite, Date: Unknown (for purposes of examination date is assumed to be prior to filing date of Apr. 15, 2002), 2 pgs.

"Tissue-Tek DRS 2000 Automatic, Multiple Slide Stainer: Multiple with Double Quality," Article from Sakura Fintek Europe B.V., 1998, 4 pages.

"Tissue-Tek DRS 2000 Slide Stainer: Computer-Assisted Flexibility for Unmatched Productivity," Article from Sakura Finetek, U.S.A., Inc., 1998, 4 pages.

"TST Stainer Trio," Article from Mopec, Date: Unknown (for purposes of examination date is assumed to be prior to filing date of Apr. 15, 2002), 7 pgs.

(56) References Cited

OTHER PUBLICATIONS

"Varistain 24-4: Flexible, Efficient Automatic Slide Stainer," article from Shandon, Inc., 1991, 8 pages.
"Varistain 24-4K: High Throughput Continuous Slide Stainer," article from Shandon, Inc., 1991, 2 pages.
"Varistain XY Multi-Program Robotic Slide Stainer," article from Shandon, Inc., 1991, 8 pages.
"Capiliary Action Slide Stainers for Histology and Cytology," Article from Fisher Scientific, Date: Unknown (for purposes of examination date is assumed to be prior to filing date of Apr. 15, 2002), 4 pgs.
Bartusch, M. et al., "Scheduling Project Networks with Resource Constraints and Time Windows," Annals of Operations Research, vol. 16, Issue 1, Dec. 1988, pp. 201-240.
Brigati, D. J. et al., "Immunocytochemistry is Automated: Development of a Robotic Workstation Based Upon the Capillary Action Principle," The Journal of Histotechnology, vol. 11, No. 3, Sep. 1998, pp. 165-183.
Conference Proceedings Presented at the 2000 National Society for Histotechnology Convention, "An Automated In Situ Hybridization System with High Throughput Capabilities," Biogenex, 2000, 2 pages.
Critchlow, A. J., "Introduction to Robotics," MacMillan Publishing Co., New York, 1985, pp. 37-56, 151-213.
Driscoll, R. C. et al., "Analytical Systems: Discrete Automated Chemistry System with Tableted Reagents," Clinical Chemistry, vol. 29, No. 9, Apr. 21, 1983, pp. 1609-1615.
Flore, M. et al., "The Abbott IMx Automated Benchtop Immunochemistry Analyzer System," Clinical Chemistry, vol. 34, No. 9, Sep. 1988, pp. 1726-1732.
Fouda, H. G. et al., "Robotics for the Bioanalytical Laboratory: A Flexible System for the Analysis of Drugs in Biological Fluids," Trac Trends in Analytical Chemistry, Jun. 7, 1987, 10 pages.
Hamacher, V. C. et al., "Computer Organization," 2nd Edition, McGraw-Hill Book Company, New York, May 3, 1984, pp. 1-14.
Hayes, F. et al.; "A Guide to GUIs," Byte, vol. 4. Jul. 1989, pp. 250-257.
Innis, M. A. et al., "DNA Sequencing with Thermus Aquaticus DNA Polymerase and Direct Sequencing of Polymerase Chain Reaction-Amplified DNA," Proceedings of the National Academy of Sciences USA, vol. 85, Dec. 1988, pp. 9435-0440.
International Search Report for PCT/US2003/11651 (related to present application); Applicant: Ventana Medical Systems, Inc., dated Jul. 30, 2003, 2 pages.
Isenhour, T.L. et al., "Intelligent Robots—The Next Step in Laboratory Automation," Analytical Chemistry, vol. 61, No. 13, Jul. 1989, pp. 805-814.
Isenhour, T. L. et al., "Laboratory Robotics and Artificial Intelligence," Clinical Chemistry; vol. 36, No. 9, Sep. 1990, pp. 1561-1566.
Isenhour; T. L. et al., "TORTS: An Expert System for Temporal Optimization of Robotic Procedures," Journal of Chemical Information and Computer Sciences, vol. 28, No. 4, Nov. 1988, pp. 215-221.
Isenhour, T. L., "Robotics in the Laboratory," Journal of Chemical Information and Computer Sciences, vol. 25, No. 3, Aug. 1, 1985, pp. 292-295.
Kawaba, S. et al., "Robot Task Planning System Based on Product Modeling," IEEE, 1985, pp. 471-476.
Leica ST 4040 and Leica Autostainer XL, description, Date Unknown (for purposes of examination date is assumed to be prior to filing date of Apr. 15, 2002).
Lindsey, J. S. et al., "Robotic Work Station for Microscale Synthetic Chemistry: On-Line Absorption Spectroscopy, Quantitative Automated Thin-Layer Chromatography, and Multiple Reactions in Parallel," Review of Scientific Instruments, vol. 59, No. 6, Jun. 1988, pp. 940-950.
Longnecker, D. S., "A Program for Automated Hematoxylin and Eosin Staining," Technical Bulletin of the Registry of Medical Technologies, vol. 36, No. 1, 1966, p. 19.
MaWhinney, W. H. B. et al, "Automated Immunochemistry," Journal of Clinical Pathology, vol. 43, Jun. 1, 1990, pp. 591-596.
McCahon, C. S. et al., "Job Sequencing with Fuzzy Processing Times," Computers & Mathematics with Applications, vol. 19, No. 7, Dec. 1990, pp. 31-41.
Montone, K. T. et al., "Anatomic Viral Detection is Automated: The Application of a Robotic Molecular Pathology System for the Detection of DNA Viruses in Anatomic Pathology Substrates, Using Immunocytochemical and Nucleic Acid Hybridization Techniques," The Yale Journal of Biology and Medicine, vol. 62, Mar. 1989, pp. 141-158.
Mueller N. J. et al., "Concurrent HPLC Analyses of Carbohydrate Distribution and 5-(Hydroxymethyl)-2-Furaldehyde Using Robotics," Journal of Chromatographic Science, vol. 25, May 1, 1987, pp. 198-201.
Okino, N. et al., "Robot Simulator in Tips/Geometric Simulator," Robotics and Computer Integrated Manufacturing, vol. 3, No. 4, 1987, pp. 429-437.
Plakhtin, D. L., "Use of Automatic Devices for Histological Processing and Staining of the Tissues and Certain Characterisation of Preparation of Histological Specimens," Arkh Patol, vol. 38, No. 11, 1976, pp. 76-77, Abstract Only. Accessed Jan. 14, 2004 http://www.ncbi.nlm.nih.gov).
Saiki, R. K. et al., "Enzymatic Amplification of β-Globin Genomic Sequences and Restriction Site Analysis for Diagnosis of Sickle Cell Anemia," Science, vol. 230, Dec. 20, 1985, pp. 1350-1354.
Sjolund, P. et al., "Robot Task Planning: Programming Using Interactive Computer Graphics," University of Minnesota, Apr. 1983, pp. 7-122-7-135.
Solomon, M. M. et al., "Time Window Constrained Routing and Scheduling Problems," Transportation Science, vol. 22, No. 1, Feb. 1988, pp. 1-3.
Stark, E. et al., "An Automated Device for Immunocytochemistry," Journal of Immunological Methods, vol. 107, Feb. 24, 1988, pp. 89-92.
Stelzner, M. et al., "The SimKit System: Knowledge-Based Simulation and Modeling Tools in Kee," An Intellicorp Technical Article, 1987, 22 pages.
Stross, W. P. et al., "Automation of APAAP Immunocytochemical Technique," Journal of Clinical Pathology, vol. 42, Jan. 1989, pp. 106-112.
Unger, E. R. et al., "Colorimetric In-Situ Hybridization in Clinical Virology: Development of Automated Technology," Current Topics in Microbiology and Immunology, vol. 143, 1989, pp. 21-31.
Unger, E. R. et al., "Viral Diagnosis by In Situ Hybridization: Description of a Rapid Simplified Colometric Method," The American Journal of Surgical Pathology, vol. 10, No. 1, Jan. 1986, pp. 1-8.
Viglierchio, D.R., et al., "Automatic Solvent Exchanger," Transactions of the American Microscopical Society 84, Department of Nematology, University of California, Davis, Apr. 1965, pp. 284-293.

* cited by examiner

APPARATUSES FOR HEATING MICROSCOPE SLIDES CARRYING SPECIMENS

CROSS REFERENCE TO RELATED APPLICATIONS

This application is a continuation of U.S. application Ser. No. 16/010,357, filed Jun. 15, 2018 (U.S. Pat. No. 10,429,280), which is a continuation of U.S. application Ser. No. 13/128,856, filed May 11, 2011 (U.S. Pat. No. 10,184,862), which is a National Phase Application of PCT Application No. PCT/US2009/064235, filed Nov. 12, 2009, which claims priority to U.S. Provisional Patent Application No. 61/113,964, filed Nov. 12, 2008, which are all hereby incorporated by reference in their entireties.

TECHNICAL FIELD

The present invention relates generally to methods and apparatuses for processing slides carrying specimens. More specifically, the invention is related to adhering specimens onto microscope slides.

BACKGROUND

Tissue analysis is a diagnostic tool used by physicians, such as pathologists, to diagnose different types of illnesses and by medical researchers to obtain information about pathology, tissue composition, and tissue architecture. A wide range of different procedures are commonly used to prepare a tissue sample for tissue analysis. Many types of tissue are relatively soft and pliable and, thus, not suitable for sectioning. Techniques for preparing tissue samples include fixing the tissue, embedding the tissue in a material, sectioning the embedded tissue, and transferring the tissue sections onto microscope slides for subsequent processing and analyses, such as staining, immunohistochemistry, or in-situ hybridization. To section a tissue sample for optical microscope examination, a relatively thin strip of tissue can be cut from a large tissue sample so that light may be transmitted through the thin strip of tissue. An average thickness of the strip of tissue is often on the order of about 2 microns to about 8 microns.

Water is often used to facilitate transfer of the thin strips of tissue onto microscope slides. A residual droplet of water trapped between the microscope slide and the thin strips of tissue will cause the thin strips of tissue to float on the slide. The floating tissue sections of these wet slides are susceptible to movement along the front surface of the microscope slides. If the tissue samples move too far, the samples may fall off of the microscope slide. If the physician is unaware of the sample falling off of the microscope slide, a diagnosis may be made based on an incomplete test result, which may ultimately contribute to a misdiagnosis. For example, if a set of tissue samples are floating on residual water on a slide, one of the tissue samples may fall off the slide during a drying process. The tissue sample that fell off may be a tissue sample needed for a proper diagnosis.

Horizontal hotplates and convection ovens are often used to heat and dry wet microscope slides. If a horizontal hotplate is used, it may take a relatively long period of time to evaporate the water beneath the tissue sample on a horizontally oriented slide. Additionally, the contact angle between the water and the slide often increases when embedding material of the sample melts and reaches the front surface of the slide. If the microscope slide moves or is not level during this drying process, the tissue sample may move a significant distance relative to the slide and, in some circumstances, may fall off of the microscope slide. If spaced apart tissue samples (e.g., a row of evenly spaced tissue samples) move significant distances relative to one another during the drying process, a physician may become concerned that one or more of the tissue samples fell off of the microscope slide. The physician may discard that sample-bearing slide and prepare a completely new sample-bearing slide to ensure that a complete set of tissue samples is analyzed. It may be necessary to obtain additional tissue samples from the subject. Convection ovens take a relatively long time to dry slides. Conventional convection ovens can dry vertically oriented slides in about 30 minutes to about 2 hours.

SUMMARY

At least some embodiments disclosed herein include an apparatus configured to dry a specimen on a microscope slide. The apparatus controls the temperature of a microscope slide carrying the specimen. The apparatus heats the specimen while the microscope slide is held in a position that both facilitates adhesion between the specimen and the slide and controls movement of the specimen, if any, relative to the microscope slide.

The apparatus, in some embodiments, holds the microscope slide in a near vertical orientation to limit, minimize, or substantially prevent movement of the specimen relative to the microscope slide. The specimen can remain at the same general position relative to the microscope slide before and/or during a drying process. In certain embodiments, the specimen is adhered to an area of the slide over which the specimen was originally placed. Additionally, residual transfer fluid between the specimen and the slide drains so as to bring the specimen into physical contact with the slide, thereby reducing drying time. The specimen can be heated to couple a back surface of the specimen to a front surface of the slide.

In some embodiments, a dryer is adapted to hold a carrier in an upright position to allow residual transfer fluid between a specimen and the carrier to move away from an interface between the specimen and the carrier. A conductive heater of the dryer is capable of generating a sufficient amount of heat for conductively heating at least a portion of the specimen to a melt point. The specimen includes a biological sample of tissue and another material, such as an embedding material with a relatively low melt point. The melted embedding material can be cooled to fixedly couple the specimen to the carrier. In certain embodiments, the carrier is a slide, such as a microscope slide.

The conductive heater supports and delivers heat to a back surface of the carrier such that heat is conducted across the thickness of the carrier to the specimen on a front surface of the carrier. At least a portion of the embedding material is melted. The melted portion of the embedding material allows the specimen to physically contact the front surface of the carrier. When cooled, the specimen is securely attached to the front surface of the carrier.

In some embodiments, an apparatus for processing a microscope slide carrying a specimen includes a slide dryer. The specimen can include a biological sample and an embedding material. The slide dryer can dry the specimen and embedding material without unwanted migration of the biological sample. In some embodiments, the slide dryer is configured to hold a microscope slide in a substantially vertical orientation. The slide dryer includes a controller and a conductive slide heater communicatively coupled to the controller. The conductive slide heater is adapted to generate a sufficient amount of heat in response to a signal from the controller so as to conductively heat the specimen on the microscope slide to a melt point of the embedding material. The slide dryer can efficiently dry the microscope slide even if the surrounding ambient temperature is relatively low, for example, at room temperature.

In some embodiments, a slide dryer is configured to hold the microscope slide in a vertical orientation while the wet mount microscope slide is dried. A conductive slide heater selectively heats the microscope slide and biological sample carried thereon to adhere the biological sample to the microscope slide.

In other embodiments, a slide dryer includes a conductive slide heater that has an engagement face and an angle of inclination of about at least 75 degrees. The conductive slide heater is adapted to heat the engagement face to a temperature equal to or greater than about 50 degrees Celsius.

In some embodiments, an apparatus for processing a microscope slide includes a drying station, a processing station, and a transport device. In some embodiments, the drying station includes a slide dryer configured to hold a microscope slide in a substantially vertical orientation and to generate heat for conductively heating at least one specimen carried by the microscope slide for a period, such as a drying period. The processing station is adapted to process the specimen on the microscope slide after the drying period. The transport device is configured to transport microscope slides between the slide dryer and the processing station.

In some embodiments, a method for processing a specimen on a microscope slide is provided. The method includes positioning the specimen on a microscope slide such that residual transfer fluid is between the specimen and the microscope slide. The microscope slide is held in a substantially vertical orientation to urge the residual transfer fluid from between the specimen and the microscope slide. The microscope slide is conductively heated while the microscope slide is in the substantially vertical orientation using a conductive slide heater that physically engages the microscope slide.

In other embodiments, a method for processing a specimen carried by a microscope slide includes positioning a microscope slide carrying a specimen in a substantially vertical orientation. The specimen floats on residual transfer fluid trapped on the microscope slide. The residual transfer fluid is drained from between at least a portion of the floating specimen and the microscope slide. The microscope slide is conductively heated using a conductive slide heater.

A slide dryer, in some embodiments, can dry a microscope slide generally independent of a temperature of the ambient air. Heat can be conductively delivered to the microscope slide to rapidly heat the microscope slide generally independent of the surrounding air temperature. A user can easily access the slide dryer to manually load microscope slides onto the slide dryer and to remove the microscope slides after a drying period. In some embodiments, the slide dryer can have a controller that can be programmed to perform different types of drying processes.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

DETAILED DESCRIPTION

Figure 1:
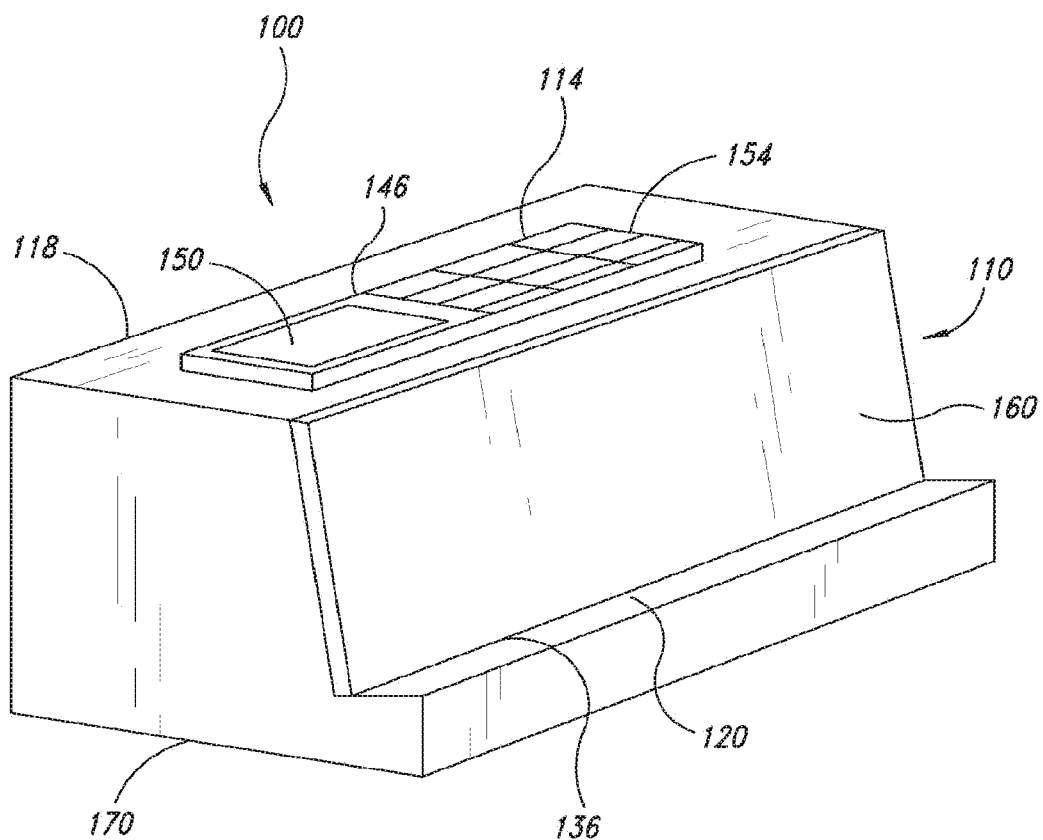
FIG. 1 is a pictorial view of a slide dryer for heating microscope slides, in accordance with one embodiment.

FIG. 1 shows a slide dryer 100 capable of drying one or more specimen-carrying microscope slides. The slide dryer 100 can heat the microscope slides and specimens carried thereon in order to dry the slides and/or specimens, to couple the specimens to the slides, and/or to perform any other desired thermal processing. The specimen-carrying microscope slides are held in an orientation that promotes removal of residual transfer fluid between the specimens and the respective microscope slides while limiting, minimizing, or substantially eliminating unwanted movement of the specimens. The specimen-carrying slides are dried to fixedly couple the specimens to the respective slides. After the specimens are fixedly coupled to the slides, the specimen-carrying slides are removed from the slide dryer 100 for subsequent processing and tissue analyses, such as staining, immunohistochemistry, in-situ hybridization, or other processing. The illustrated slide drying 100 is portable and can be readily carried (e.g., manually transported) by a person. In a laboratory setting, the slide dryer 100 can be manually transported between workstations.

The microscope slides can be held in substantially vertical orientations to promote removal of residual transfer fluid trapped beneath the specimens to reduce drying times. A region of a slide beneath a specimen can be rapidly dried by draining flowable residual transfer fluid away from the specimen. As such, only a portion of the residual transfer fluid is evaporated to dry the region of the slide facing the specimen. The slide dryer 100 produces heat to both dry the slides and facilitate coupling of the specimens to the slides. The specimens can include, without limitation, a biological sample (e.g., a tissue sample) and a material (e.g., an embedding material) in which the sample is embedded.

At least a portion of the embedding material is melted, brought into contact with the slide, and solidified so as to attach the biological sample directly to the slide. The embedding material can move towards the microscope slide and can be ultimately deposited on the slide. If that material is more hydrophobic than the material of the slide and the residual transfer fluid (e.g., water), the embedding material may promote beading of the fluid. As the embedding material coats the slide, a contact angle between the fluid and slide will increase. Because the microscope slide is in the upright orientation, the residual transfer fluid will tend to accumulate at a lower end of the specimen due to gravity. An upper end of the specimen can physically contact the front face of the slide and minimize, limit, or substantially prevent unwanted migration of the specimen. After a sufficient amount of residual transfer fluid has accumulated, it can drain downwardly away from the specimen, thereby leaving the specimen on the front face of the slide. This process can be performed on a wide range of wetted microscope slides.

The illustrated slide dryer 100 of FIG. 1 includes a conductive slide heater 110, a controller 114, and a main body 118 that houses internal components of the slide dryer 100. The conductive slide heater 110 can physically contact and support one or more microscope slides. The main body 118 includes a slide support 120 adjacent to the conductive slide heater 110.

The conductive slide heater 110 and slide support 120 can cooperate to hold a microscope slide in a substantially vertical orientation such that heat generated by the conductive slide heater 110 is transferred to the microscope slide for a desired period, such as a drying period. The conductive slide heater 110 is capable of generating a sufficient amount of heat in response to a signal from the controller 114 so as to conductively heat the specimen to a desired temperature. Residual transfer fluid can flow away from the specimen, evaporate, and/or otherwise be removed from the specimen-carrying microscope slide. The heated specimen is brought into physical contact with the microscope slide. The specimen can be elevated to a temperature that facilitates adhesion between the specimen and the microscope slide, as discussed in connection with FIGS. 6-9.

Figure 2:
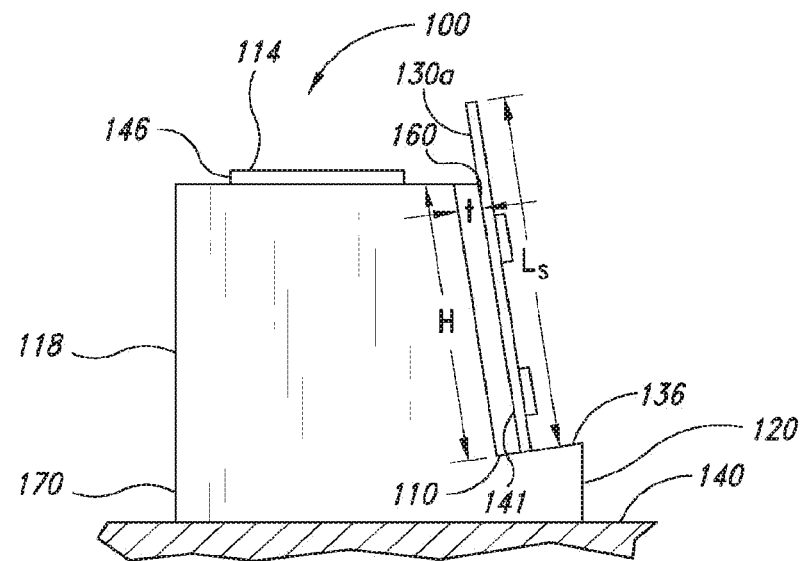
FIG. 2 is a side elevational view of the slide dryer of FIG. 1 holding a plurality of specimen-carrying microscope slides.
Figure 3:
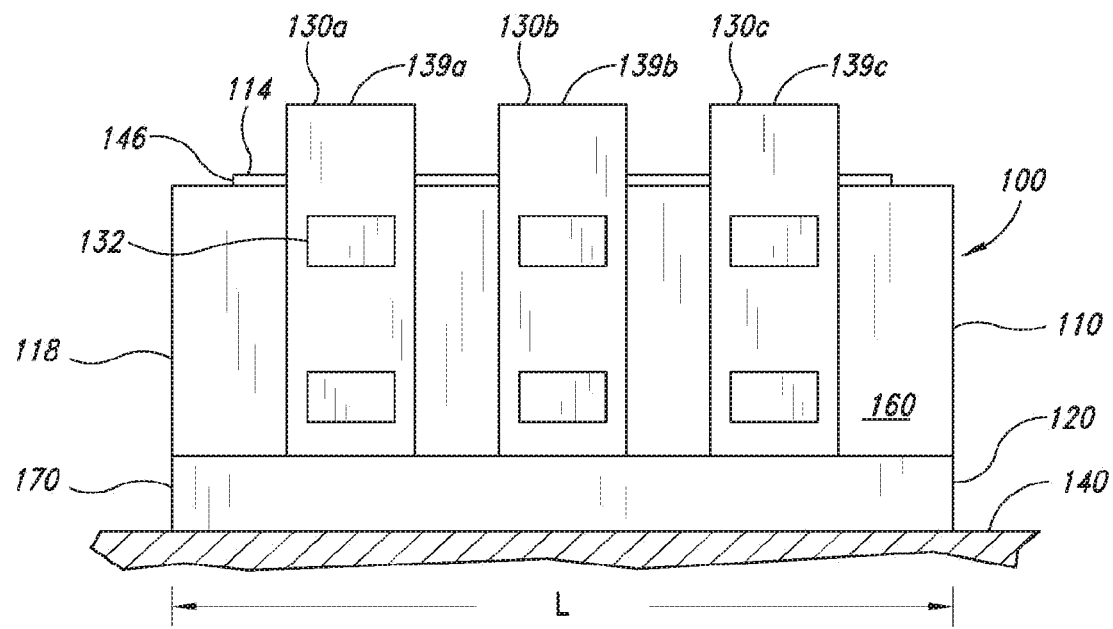
FIG. 3 is a front elevational view of the slide dryer and specimen-carrying microscope slides of FIG. 2.

FIGS. 2 and 3 show a plurality of microscope slides 130a, 130b, 130c (collectively 130) resting against the conductive slide heater 110 and on an upper surface 136 of the slide support 120. The microscope slides 130 can be generally flat transparent substrates carrying specimens 132 for examination using equipment, such as optical equipment (e.g., a microscopic). For example, each microscope slide 130 may be a generally rectangular piece of a transparent material (e.g., glass) having a front face for receiving specimens and a back face for engaging the slide dryer 100. The microscope slides 130 may be charged or uncharged depending on the application and can have a wide range of different dimensions. In some embodiments, the slides 130 have a length of about 3 inches (75 mm) and a width of about 1 inch (25 mm) and, in certain embodiments, may include a label, such as a barcode. In some embodiments, the slides have a length of about 75 mm, a width of about 25 mm, and a thickness of about 1 mm. The microscope slides 130 can be in the form of standard microscope slides. The illustrated microscope slides 130 carry the uncovered specimens 132 (e.g., without coverslips). In some embodiments, the dimensions of slide support 120 are such that a label on a slide 130 is located on a face of the slide opposite the slide support and above the portion of the slide that is in contact with the slide support. In this manner, the label can be protected from heat during the drying process.

The main body 118 rests on a generally horizontal support surface 140 such that the microscope slides 130 are held generally upright. The controller 114 may be conveniently accessed by a user to control operation of the slide dryer 100. FIGS. 1-3 show the controller 114 communicatively coupled to the conductive slide heater 110 including a housing 146, a display 150, and an input device 154. The display 150 can be a screen or other display device. The input device 154 can include, without limitation, one or more buttons, keyboards, input pads, buttons, control modules, or other suitable input elements. The illustrated input device 154 is in the form of an input pad, such as a touch pad, used to program the slide dryer 100.

The controller 114 can generally include, without limitation, one or more central processing units, processing devices, microprocessors, digital signal processors, central processing units, processing devices, microprocessors, digital signal processors (DSP), application-specific integrated circuits (ASIC), readers, and the like. To store information (e.g., a drying program), the controller 114 can also include, without limitation, one or more storage elements, such as volatile memory, non-volatile memory, read-only memory (ROM), random access memory (RAM), and the like. The controller 114 can be programmed based on the desired processing of the specimen-carrying slides. In a fixed temperature mode of operation, the controller 114 is used to maintain the conductive slide heater 110 at a generally constant temperature. In a variable temperature mode of operation, the controller 114 is used to adjust the temperature of the conductive slide heater 110. The controller 114 can store one or more programs for controlling the operation of the conductive slide heater 110. The input device 154 can be used to switch between different programs, modes of operation, or the like.

Referring to FIGS. 1-3, heat can be efficiently transferred across the thicknesses of the microscope slides 130. The illustrated conductive slide heater 110 of FIG. 2 has a height H that is greater than or equal to the lengths of specimen mounting regions of the slides 130. A substantial portion of a longitudinal length $L_s$ of each microscope slide 130 can contact the conductive slide heater 110 to facilitate generally even heat distribution throughout the entire mounting regions. In some embodiments, the height H is at least about 2.5 inches (63.5 mm), about 2.75 inches (70 mm), or about 2.9 inches (74.7 mm), as well as ranges encompassing such heights. Upper ends 139a, 139b, 139c of the slides 130a, 130b, 130c, respectively, can protrude upwardly past the slide dryer 100 for conveniently grasping the slides 130.

A longitudinal length L of the conductive slide heater 110 can be selected based on the desired number of microscope slides 130 to be processed. The length L can be increased or decreased to increase or decrease the number of microscope slides that can be processed, spacing between the microscope slides, or the like. The illustrated embodiment of FIG. 3 has three spaced apart microscope slides 130. In some embodiments, the length L is at least 6 inches (152 mm) to allow at least three microscope slides 130 to be concurrently processed. Other dimensions are also possible.

The conductive slide heater 110 can be a plate having a generally rectangular shape, as viewed from the side (see FIG. 3). The thermal properties of the conductive slide heater 110 may be selected based on desired processing criteria, such as the desired processing temperature, temperature distribution, rates of heating/cooling, and the like. For example, an engagement face 160 of the slide heater 110 can have a relatively low thermal mass and a high thermal conductivity for rapidly transferring heat across the entire face 160. The engagement face 160 can have a substantially uniform heat distribution to ensure that all or most of the slides 130 are maintained at substantially the same temperature.

The conductive slide heater 110 can be made, in whole or in part, of one or more thermally conductive materials, for example, metals such as copper, steel, aluminum, iron, combinations thereof, or the like. In some embodiments, the engagement face 160 is made mostly of steel (e.g., stainless steel) and is highly resistant to wear and corrosion. In other embodiments, the engagement face 160 is made mostly of copper for rapidly transferring heat between internal heating elements and the slides 130. Advantageously, the number of internal heating elements, such as resistive heaters of the heater 110, can be reduced because of this rapid heat transfer. The conductive slide heater 110 can have a multi-layer construction to enhance wear characteristics and thermal performance. For example, the engagement face 160 can be a thin sheet of steel, and an inner layer of copper in the heater 110 can help distribute and deliver heat to the face 160. In other embodiments, the conductive slide heater 110 has a monolayer construction.

The engagement face 160 can be substantially flat to increase the areas of contact between the slides 130 and the face 160. The engagement face 160 can be a highly polished face that is extremely flat for contacting most or substantially all of overlying portions of the slides 130. In some embodiments, the engagement face 160 is configured to minimize, limit, or substantially prevent relative movement of the microscope slides 130. For example, anti-migration features (e.g., protrusions, protuberances, grooves, partitions, texturing, and the like) can be incorporated into the face 160.

The main body 118 of FIGS. 1-3 has a base 170 for resting on the surface 140. The main body 118 protects internal components, even when the slide dryer 100 is used in harsh environments, including, without limitation, corrosive environments often found in labs, or other testing sites. The slide support 120 is integrally formed with the main body 118. In the illustrated embodiment, the upper surface 136 extends generally perpendicularly with respect to the engagement face 160. When the lower ends of the microscope slides 130 rest upon the upper surface 136, the back surfaces 141 of the slides 130 (see FIG. 2) lie flat against the engagement face 160.

Figure 4:
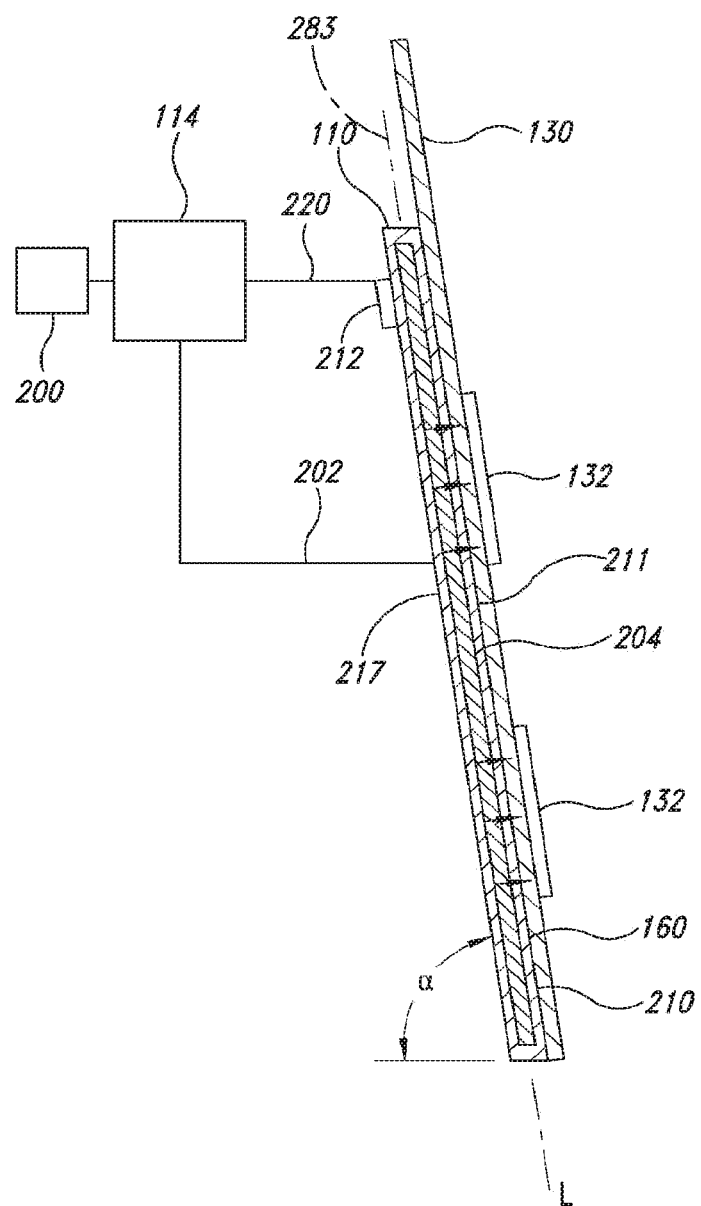
FIG. 4 is a partial cross-sectional view of components of a slide dryer and a specimen-carrying microscope slide.

FIG. 4 shows the controller 114, a power source 200, a line 202 that delivers electrical power to the conductive slide heater 110, and a sensor 212 for evaluating operation of the slide heater 110. A line 220 communicatively couples the controller 114 to the sensor 212. The illustrated conductive slide heater 110 includes an outer portion 210 and a thermo-electric element 204. The term "thermo-electric element" is a broad term that includes, without limitation, one or more electric devices capable of generating heat and/or absorbing heat.

Substantially all or most of the engagement face 160 can have a substantially uniform temperature when the element 204 is activated. For example, substantially all or most of the engagement face 160 can be within a temperature range of about 10 degrees Celsius. In certain embodiments, the engagement face 160 is maintained at generally the same temperature. For example, the average temperature of the engagement face 160 can be in a range of about 5 degrees Celsius. In other embodiments, different portions of the engagement face 160 can be maintained at different temperatures to accommodate drying of slides holding different types of tissues and for tissues embedded with different embedding materials.

In some embodiments, including the illustrated embodiment of FIG. 4, the outer portion 210 is a hollow plate, and the thermo-electric element 204 is a heating element adapted to convert electrical energy to thermal energy. When the heating element 204 generates heat, heat is transferred through the portion 210 and is absorbed by the microscope slide 130. Heat is ultimately transferred from the slide 130 to the specimens 132. The amount of electrical energy delivered to the element 204 can be increased or decreased to increase or decrease the temperature of the specimens 132.

The heating element 204 can be a resistive heating element. A wide range of different types of resistive heating elements (e.g., plate resistive heaters, coil resistive heaters, strip heaters, or the like) can be selected based on the desired operating parameters. Other types of thermal elements, such as cooling elements, heating/cooling elements, or the like, can be utilized. As used herein, the term "cooling element" is a broad term that includes, without limitation, one or more elements capable of actively absorbing heat so as to effectively cool at least a portion of the conductive slide heater 110. For example, a cooling element can be a cooling tube or channel through which a chilled fluid flows. In some embodiments, the conductive slide heater 110 includes heating elements for producing heat during a heating period and cooling elements for absorbing heat during a cooling period.

In some embodiments, the element 204 is a heating/cooling element, such as a Peltier device. Peltier devices may be solid state components which become hot on one side and cool on an opposing side, depending on a direction of current passed therethrough. By simply selecting the direction of current, the Peltier device 204 can be employed to heat the engagement face 160 for a desired length of time. By switching the direction of the current, the device 204 cools the engagement face 160. In other embodiments, the heating/cooling element 204 can be in the form of channels through which a working fluid flows. Heated fluid can be passed through the channels for a heating period, and a chilled fluid can be passed through the channels for a cooling period. The position, number, and type of heating/cooling elements 204 can be selected based on the desired temperature profile of the conductive slide heater 210.

The thermal properties of the portion 210 can be selected to achieve a desired temperature distribution along a wall 211 of the engagement face 160. For example, the portion 210 can be made, in whole or in part, of a highly conductive material, such as copper, or other suitable material with sufficient thermal conductivity to reduce or limit any significant local temperature non-uniformities associated with discrete heating elements 204. Because heat is lost to the surrounding air (e.g., air at room temperature), the elements 204 can continually produce a constant flux. The interior portions of the slide heater 110 may be hotter than the periphery of the heater 110 because heat is dissipated faster from the periphery of the slide heater 110 due to its exposed edges. In some embodiments, an array of closely spaced heating elements 204 is used to maintain a generally uniform temperature across the surface 160. Other configurations are also possible.

The sensor 212 is a temperature sensor that detects the temperature of the heater 110 and sends one or more signals indicative of that temperature. The sensor 212 can be mounted on a back surface 217 of the conductive slide heater 110, embedded in the heater 110, mounted on or embedded in the engagement face 160, or positioned at any other suitable location for measuring the temperatures of any portion of the slide heater 110 and/or the microscope slides 130. The sensor 212 can include, without limitation, one or more thermal couples, thermometers (e.g., an IR thermometer) pyrometers, resistance temperature detectors (RTDs), thermistors, or the like.

Figure 5:
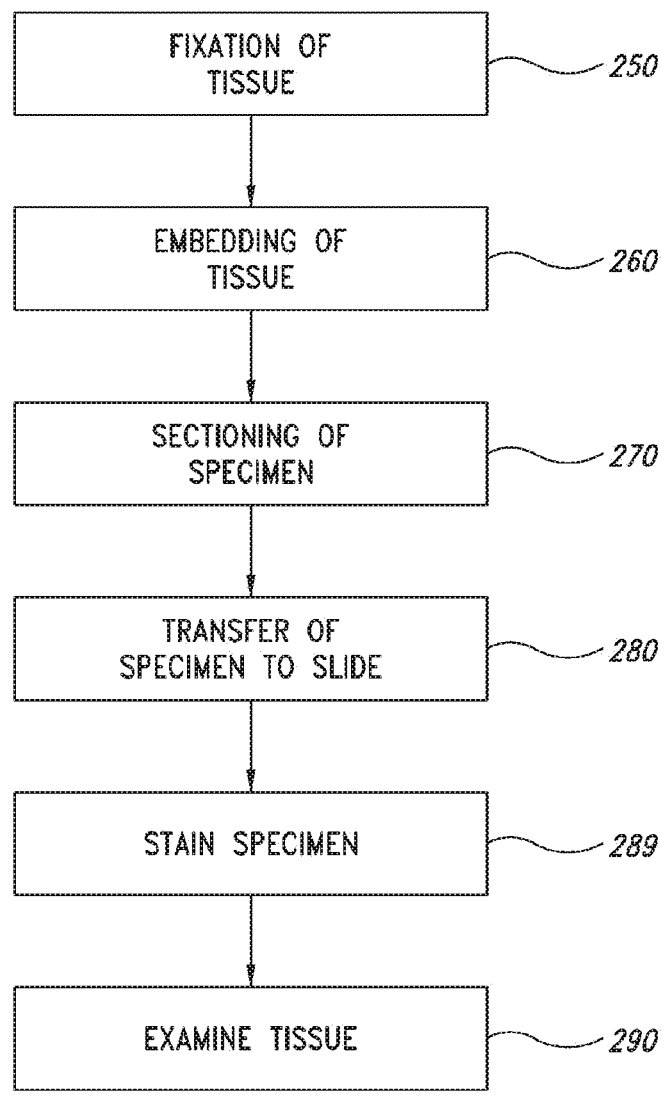
FIG. 5 is a flow chart of one method of processing a biological sample.

FIG. 5 is a flow diagram of one method of preparing and analyzing a specimen. Generally, a specimen can be placed on a microscope slide using a thin tissue section transfer fluid such as water. The specimen-carrying microscope slide is loaded into the slide dryer and dried such that the specimen is adhered to the microscope slide. The slide dryer 100 rapidly dries the slide while minimizing, limiting, or substantially eliminating unwanted migration of the specimen relative to the microscope slide. The specimen can remain at the same general position relative to the slide during the drying process. If a plurality of specimens is mounted on the slide, the spacing between the specimens can be maintained throughout the drying process. This may reduce or eliminate a physician's concern about tissue specimens falling off of the microscope slide. The specimen-carrying slide can then be conveniently transported and analyzed using a wide range of different examination techniques and equipment. This process is discussed in detail below.

A biological sample, such as a sample of tissue, is processed to preserve its characteristics, such as the tissue structure, the cell structure, and the like. The tissue can be any collection of cells mountable on a microscope slide including, without limitation, a section of an organ, tumor section, bodily fluid, smear, frozen section, cytology prep, or cell lines. For example, the tissue sample can be a sample obtained using an incisional biopsy, a core biopsy, an excisional biopsy, a needle aspiration biopsy, a core needle biopsy, a stereotactic biopsy, an open biopsy, a surgical biopsy, or the like.

At 250, a fixative is used to fix and preserve the sample. Fixatives can fix and preserve cellular structure, inhibit or substantially stop enzymatic action that may result in the purification or autolysis of the tissue, or the like. The fixation process can increase the rigidity of the tissue, thereby making it more convenient to section, as detailed below. Formaldehyde, ethanol, acetone, paraformaldehyde, or other types of fixatives can be used. The type and number of fixatives can be selected based on the desired processes to be performed, such as staining, cytological staining, immunohistochemistry, or in-situ hybridization. After fixing the tissue sample, the tissue sample can be stored for a desired length of time.

At 260, the sample is embedded in a material that has mechanical properties that may facilitate sectioning. Materials for embedding include, but are not limited to, paraffin, resin (e.g., plastic resins), polymers, agarose, nitrocellulose, gelatin, mixtures thereof, or the like. In some embodiments, the embedding material comprises mostly or entirely of paraffin. Paraffin is a white or generally colorless water insoluble solid substance that is resistant to many reagents. For example, paraffin can be a mixture of hydrocarbons chiefly of the alkaline series obtained from petroleum. A wide range of different mixtures of similar hydrocarbons can be used to make paraffin, and these mixtures can be solid, semi-solid, and/or oily. In some embodiments, the paraffin is a wax.

A wide range of different conventional impregnating processes can be used to at least partially embed material in the tissue sample. The tissue samples can be mixed or combined with material that can permeate the tissue sample so as to impart properties that facilitate a cutting process. In this manner, the tissue samples are embedded. If the tissue sample is to be sectioned with a microtome or similar device, the tissue sample can be embedded in paraffin or other suitable material, such as a plastic resin. If the embedding material is paraffin, the paraffin can be heated and melted. The hot liquid paraffin at least partially impregnates the biological sample and is subsequently solidified.

At 270, the specimen is cut into mountable sections, placed on a microscope slide, and then dried. A microtome can cut the specimen into thin sections, for example, slices on the order of about 5 microns to about 6 microns thick. Each section can include a portion of the tissue sample and some of the embedding material.

Different techniques can be used to transfer the tissue specimens onto the microscope slide at 280. In some embodiments, the cut sections are floated on water to spread or flatten the sections. If the sections are pieces of paraffin embedded tissue, the sections can be floated on a warm bath to keep the sections in generally flat configurations, thereby reducing or preventing folding, creasing, or bending. A microscope slide is inserted into the warm bath. A front surface of the slide is used to pick up the tissue specimens. To examine multiple tissue samples (e.g., a set of tissue samples, each taken at a different location of a subject) using a single slide, a plurality of the tissue samples may be sequentially floated onto the slide. These wet slides are then dried using the slide dryer 100.

Figure 6:
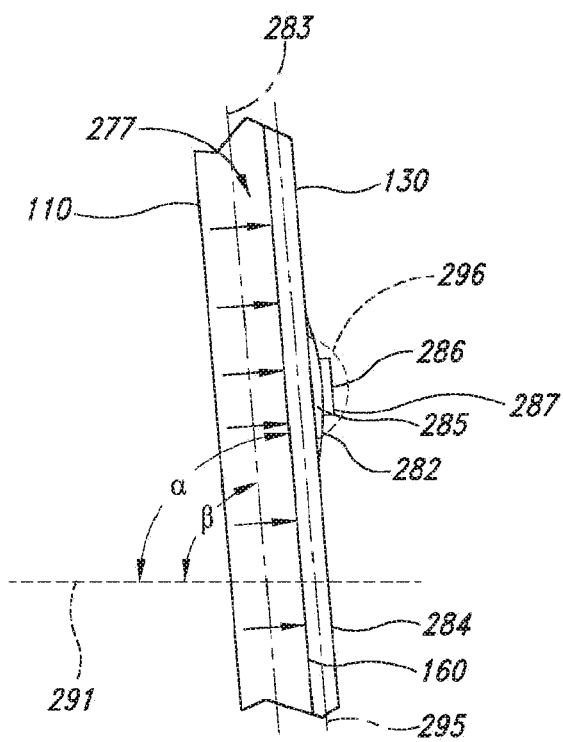
FIG. 6 is an elevational view of a specimen and residual transfer fluid positioned on a microscope slide supported by a conductive slide heater.

FIG. 6 shows a specimen 286 positioned on a droplet of transfer fluid 282. The droplet of transfer fluid 282 can be water or other suitable fluid (including aqueous mediums) that may or may not contain any additives (e.g., wetting agents, reagents, dyes, etc.). If water is employed, the water may be de-ionized water, double-distilled de-ionized water, purified water, or the like. The droplet of transfer fluid 282 can be formed as the slide 130 is pulled out of the bath as described above. Alternatively, the droplet 282 can be deposited by directly dropping the transfer fluid onto the front surface 284 and thereafter placing the specimen on top of the droplet. A droplet placed directly onto surface 284 then functions to allow positioning of the specimen on the front surface 284. The contact angle between the transfer fluid 282 and the slide 130 is relatively small so that the specimen 286 is kept at the same general location, even if the slide 130 is moved between, for example, workstations or different equipment.

The surface tension of the transfer fluid 282 helps maintain a generally flat configuration of the specimen 286 to limit, reduce, or substantially prevent unwanted irregularities of the specimen 286, such as folding, creasing, protruding, buckling, or the like. Because the fluid 282 is trapped between the specimen 286 and the microscope slide 130, the specimen 286 is kept away from the front surface 284.

The microscope slide 130 is held in a substantially vertical orientation to promote draining of the fluid 282 to reduce drying times. The illustrated slide 130 is at an angle of inclination $\alpha$ defined by a generally horizontal imaginary plane 291 (e.g., an imaginary plane generally parallel to the support surface 140 of FIGS. 2 and 3) and the engagement face 160. Because the slide 130 lays flat against the conductive slide heater 110, the slide 130 is held at the same general angle of inclination. The illustrated conductive slide heater 110 extends generally along an imaginary plane 283 that defines an angle $\beta$ with the imaginary horizontal plane 291 that is greater than about 70 degrees, 80 degrees, 85 degrees, or 90 degrees. A longitudinal axis 295 of the slide 130 is generally parallel to the imaginary plane 283. The angle β can be equal to or greater than about 80 degrees to keep the microscope slide 130 at an angle of inclination α of about 80 degrees. Other angles are also possible, if needed or desired.

The engagement surface 160 is maintained at or above a melt point of the embedding material of the specimen 286 in order to conductively heat the specimen 286. If the embedding material is paraffin with a melt point between about 50 degrees Celsius and 57 degrees Celsius, the surface 160 is kept at or above a temperature of about 50 degrees Celsius. Arrows 277 represent heat being transferred from the heater 110 to the specimen 286. When the embedding material melts, the melted material may float along the upper surface of the transfer fluid 282 and become deposited on the front surface 284. If the embedding material is more hydrophobic than the microscope slide 130, the contact angle at which the transfer fluid 282 interfaces with the surface 284 may increase, thereby causing the fluid 282 to form an unstable droplet susceptible to migration along the surface 284. The tilted slide 130 promotes accumulation of the transfer fluid 282 proximate a lower portion 287 of the specimen 286. The fluid 282 collects at a gap 285 between the specimen 286 and the microscope slide 130 such that the fluid 282 eventually drains down the front surface 284.

Figure 7:
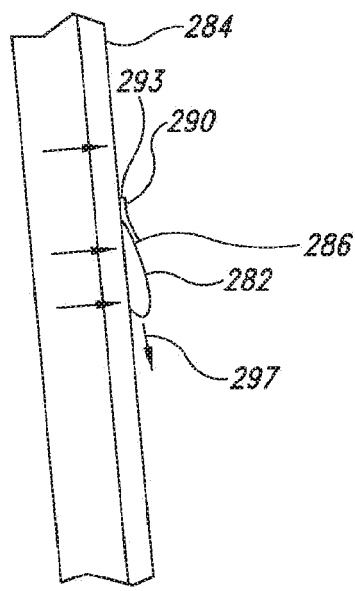
FIG. 7 is an elevational view of a specimen-carrying microscope slide before a back surface of a specimen is adhered to a front face of the slide.

FIG. 6 also shows a position 296 (shown in phantom line) of the fluid 282 after the contact angle has increased assuming the microscope 130 was in a horizontal orientation instead of the vertical orientation. Because the illustrated microscope slide 130 is at an upright orientation, the fluid 282 tends to accumulate at the gap 285 due to gravity, as shown in FIG. 7. An upper portion 293 of the specimen 286 can physically contact the heated surface 284 to limit, minimize, or substantially prevent migration of the specimen 286. The upper portion 293, for example, may stick to the surface 284.

After a sufficient amount of fluid 282 has accumulated, it has a tendency to drain downwardly away from the specimen 286, as indicated by the arrow 297. The fluid 282 flows downwardly away from the specimen 286 and travels down the surface 284. In this manner, at least a portion or substantially all of the fluid 282 trapped between the specimen 286 and the surface 284 is removed. The specimen 286 thus overlies and is in direct physical contact with the surface 284. The fluid 282 can eventually run down the entire surface 284 to the bottom end of the slide 130.

The illustrated angle of inclination of FIG. 7 is greater than about 70 degrees such that the beaded transfer fluid 282 drains after a sufficient amount of the embedding material is melted so as to appreciably increase the contact angle between the fluid 282 and the surface 284. In some embodiments, the angle of inclination is greater than about 75 degrees. Such embodiments are especially well suited to cause draining of residual transfer fluid (e.g., water) away from relatively small specimens, such as specimens containing tissue samples obtained using core needle biopsies. Residual transfer fluid can be drawn away at different speeds from different types and sizes of specimens, including relatively large specimens or small specimens. In some embodiments, the angle of inclination is greater than about 75 degrees to promote the rapid accumulation of transfer fluid 282 as the specimen 286 is heated. Once the embedding material is heated to its melt point, the transfer fluid 282 rapidly beads up and is drained therefrom.

Figure 8:
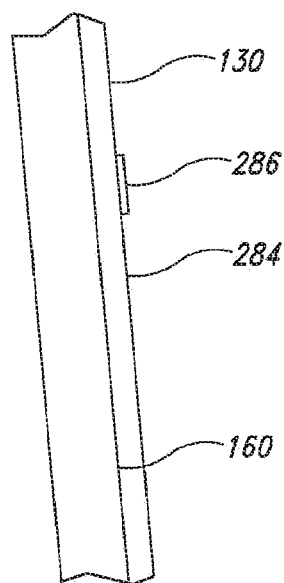
FIG. 8 is an elevational view of the specimen of FIG. 7 adhered to the microscope slide.

FIG. 8 shows the specimen-carrying slide 130 after completion of a drying period. The engagement face 160 can be maintained at a temperature equal to or greater than about 50 degrees Celsius and the ambient air can be less than 30 degrees Celsius (e.g., a temperature of about 21 degrees Celsius). The slide 130 is placed against the heater 110. The engagement face 160 heats the slide 130 such that the specimen 286 is adhered to the surface 284 in a relatively short period of time, for example, less than or equal to about 5 minutes, 1 minute, 45 seconds, 30 seconds, 20 seconds, or ranges encompassing such periods of time. Most of the transfer fluid 282 is drained away from the specimen 286 to avoid drying times associated with evaporating the entire droplet. The length of the drying period can depend on the amount of transfer fluid, the characteristics of the tissue of the specimen 286, characteristics of the embedding material, or the like.

The engagement face 160 of FIG. 7 can be maintained at or above a temperature of about 50 degrees Celsius, 55 degrees Celsius, or 65 degrees Celsius, as well as within ranges encompassing such temperatures (e.g., a range of about 50 degrees Celsius to about 65 degrees Celsius). Such temperatures are especially well suited to melt paraffin or other materials with a relatively low melt point. In some embodiments, the specimen 286 is adhered to the surface 284 in less than about 1 minute. For example, the specimen 286 can be adhered in about 10 seconds to about 1 minute. In some embodiments, the engagement face 160 is maintained at a temperature of about 65 degrees Celsius or above. In certain embodiments, the engagement face 160 can be at a temperature that is less than, greater than, or equal to about 65 degrees Celsius, 70 degrees Celsius, 80 degrees Celsius, or ranges of such temperatures. An infrared thermometer is used to measure the temperature of the engagement face 160 to maintain accuracy. The temperature of the engagement face 160 can be increased or decreased using feedback from the thermometer to decrease or increase drying times.

The engagement face 160 can be maintained at a somewhat constant temperature during the heating period for consistent drying. The slide heater 110 is thus capable of drying slides without appreciable temperature changes. By way of example, the engagement face 160 can be maintained at a generally constant temperature at or above a melt point of embedding material to ensure short drying times. In some embodiments, the temperature of the engagement face 160 is kept within an operating temperature range that is above the melt point. The operating temperature range can be 50 degrees Celsius to 60 degrees Celsius, 55 degrees Celsius to 65 degrees Celsius, or 60 degrees Celsius to 70 degrees Celsius. Other ranges are also possible.

The engagement face 160 can be pre-heated to immediately transfer heat to the slide 130 upon contact. Pre-heating can be used to avoid ramp-up times associated with cyclic heating processes. Slides can be repeatedly loaded onto the slide dryer 100 without waiting for the engagement face 160 to reach a certain temperature. Of course, the temperature of the engagement face 160 may decrease slightly as the slide 130 absorbs heat. These effects can be minimized or avoided by continuously generating heat with the slide heater 110.

In other embodiments, the engagement face 160 can be heated after the slide 130 placed against the face 160. To reduce energy consumption, the engagement face 160 can be maintained at a low temperature, for example, at about room temperature or at a temperature between room temperature and a desired temperature for drying. In some embodiments, the low temperature is a standby temperature. For example, the engagement face 160 can be kept at a standby temperature in a range of about 25 degrees Celsius to about 50 degrees Celsius. The temperature of the engagement face 160 is increased to at least about 50 degrees Celsius during or after loading of the slides 130. After drying, the engagement surface 160 returns to the standby temperature. A wide range of different types of heating cycles can be employed to reduce or limit the amount of energy used to during drying processes.

After drying, the slide 130 is removed from the slide dryer 100. To increase the rate of cooling of the specimen 286 and therefore decrease processing time, the conductive slide heater 110 can also include cooling elements (e.g., Peltier elements) used to rapidly absorb heat from the dried specimen-bearing slide 130. Once the specimen-bearing slide 130 is sufficiently cooled, it can be removed from the slide dryer 100.

At step 289, the specimen 286 is stained for examination. The specimen can also be baked, de-waxed, de-paraffinized, or the like. In some embodiments, a stain is applied to the specimen 286 after performing a de-paraffinizing process. The microscope slide is then cover slipped for subsequent optical examination.

At step 290, the specimen 286 can be examined using optical equipment (e.g., a microscope), optical instruments, or the like. Different types of examination processes can be used to perform a wide range of different tissue analyses used to obtain information about pathology, tissue composition, and the tissue architecture. This information can be used by a physician to diagnose different types of illnesses and to perform various medical research.

Figure 9:
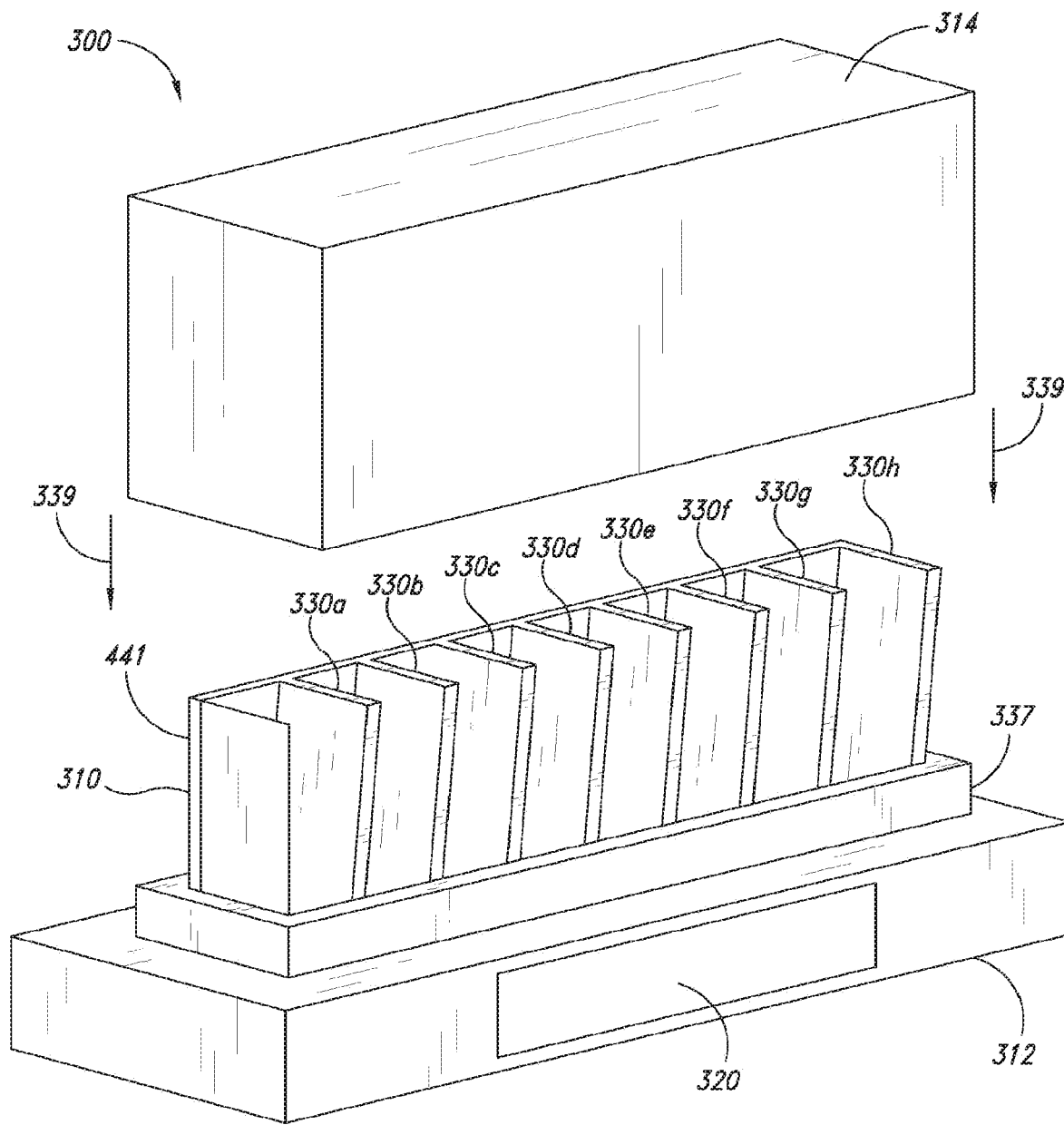
FIG. 9 is a pictorial view of a slide dryer with a cover and a conductive slide heater capable of holding a plurality of microscope slides that are spaced apart from one another.

Referring to FIG. 9, a slide dryer 300 includes a conductive slide heater 310, a base 312, and a cover 314. The base 312 includes a controller 320 for controlling operation of the conductive slide heater 310. The cover 314 can enclose and surround the conductive slide heater 310 to prevent unwanted contaminates from landing on the specimen-carrying microscope slides. The base 312 includes a collector 337 surrounding the slide conductive heater 310. The collector 337 can collect residual transfer fluid or other materials that are removed from the slides.

The illustrated conductive slide heater 310 includes a plurality of heat generating support elements 330*a-h* (collectively 330) spaced apart from one another. The support elements 330 can be independently operated or operated together and are oriented at the same or different inclines. The illustrated elements 330 are generally parallel to one another and spaced to allow at least one generally vertically oriented microscope slide to be inserted between a pair of adjacent elements 330. Each of the support elements 330 can include one or more energizable thermal devices (e.g., electro-thermal elements). In other embodiments, a back plate 441 extending between the support elements 330 has thermal devices (e.g., internal thermal devices) capable of generating heat that is conducted through the support elements 330.

In operation, microscope slides can lean against respective support elements 330. The cover 314 can be moved over the slide heater 310 as indicated by the arrows 339. The conductive slide heater 310 can dry an entire row of vertically oriented specimen-bearing microscope slides. After the microscope slides are processed, the cover 314 is removed to access and remove the microscope slides.

Figure 10:
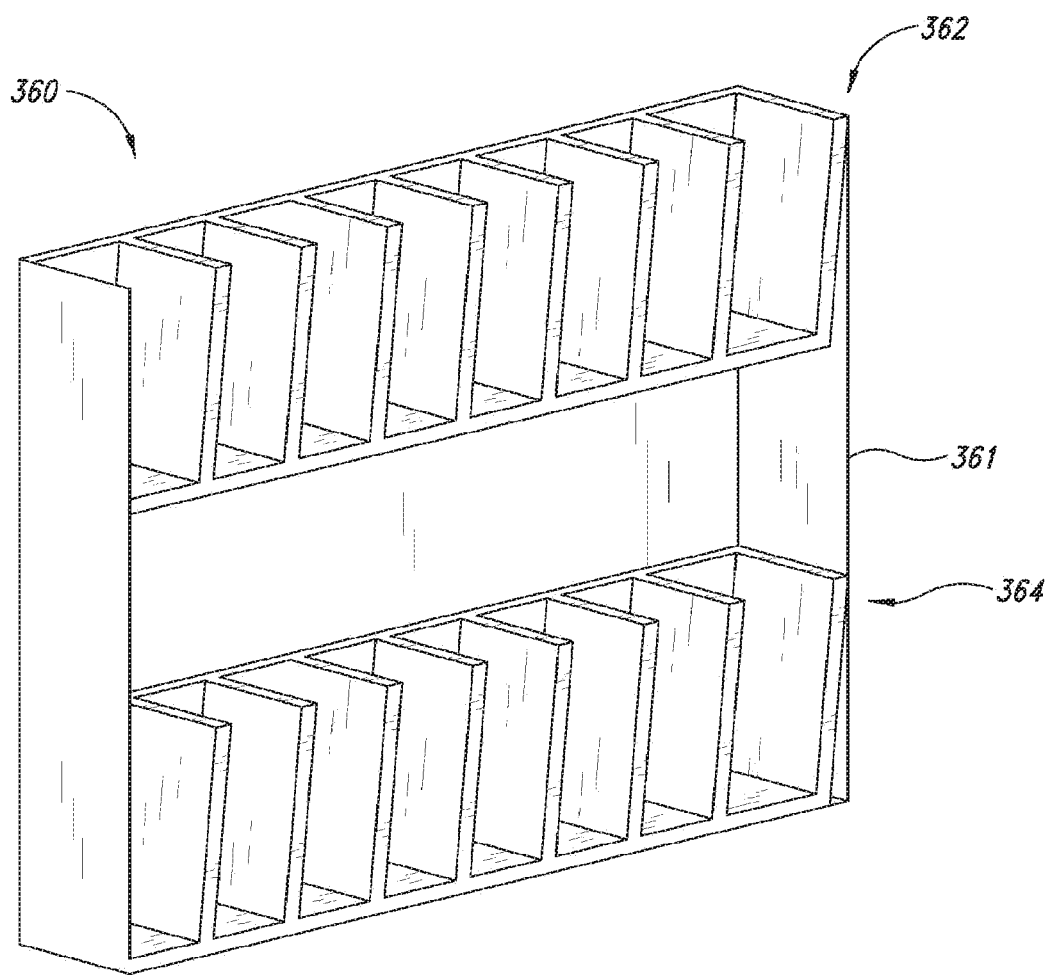
FIG. 10 is a pictorial view of a conductive slide heater for holding two rows of microscope slides.

FIG. 10 shows a heater assembly 360 that includes a frame 361 and a plurality of conductive slide heaters 362, 364 coupled to the frame 361. The conductive slide heaters 362, 364 can be generally similar to the slide conductive heater 310 of FIG. 9. The heater assembly 360 can be incorporated into different types of slide processing systems, such as an automated slide processing system or stand-alone slide dryers, and may include a controller, power sources, or the like.

Figure 11:
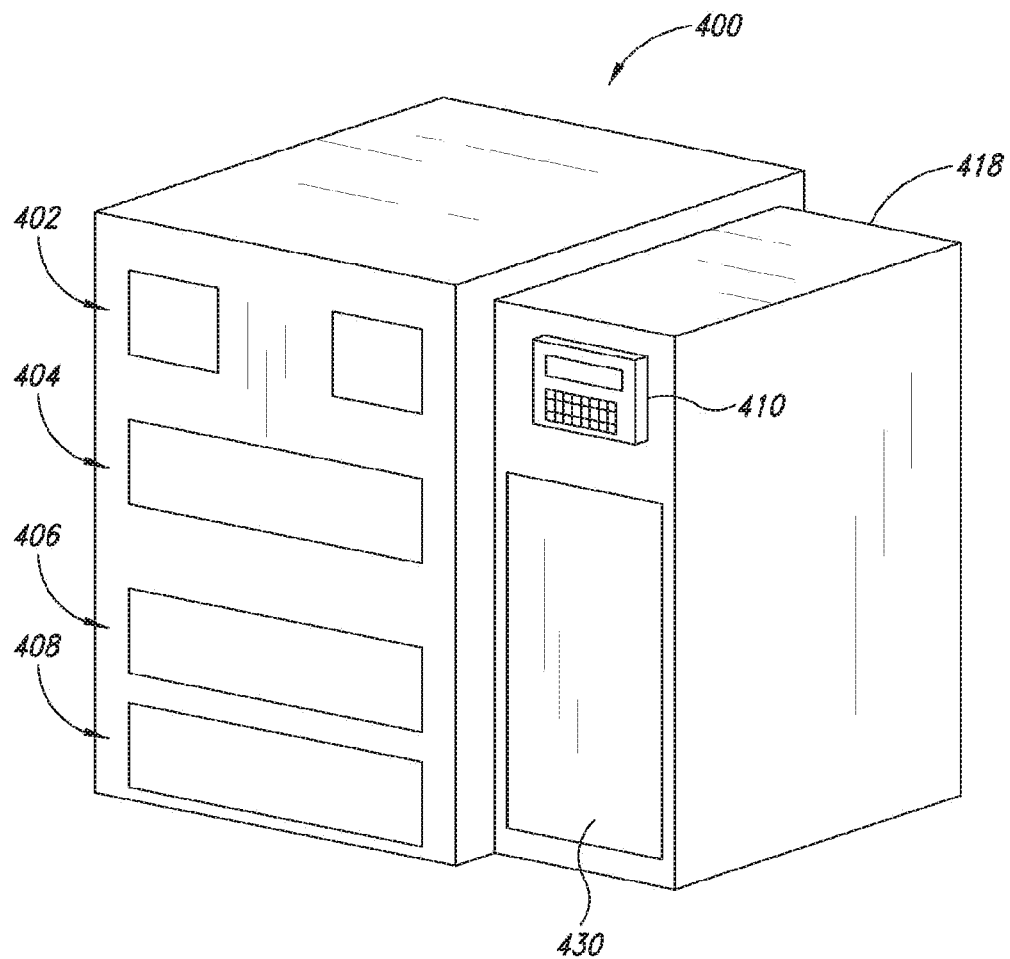
FIG. 11 is a pictorial view of an apparatus for processing microscope slides, in accordance with one illustrated embodiment.

FIG. 11 shows an apparatus 400 that includes a drying station 402 and a plurality of processing stations 404, 406, 408. A controller 410 controls operation of the drying station 402 and one or more of the processing stations 404, 406, 408. The illustrated controller 410 is communicatively coupled to and commands each of the stations 402, 404, 406, 408. Microscope slides can be automatically processed (e.g., via a process that is substantially free of human intervention) using the apparatus 400. For example, the controller 410 can control the amount of heat produced by a slide dryer 401 at the station 402 (FIG. 13), rate of drying, length of time of the drying period, or other processing parameters, preferably while keeping thermal damage to the tissue sample at or below a desired level.

As used herein, the term "processing station" includes, without limitation, a baking station, a material removal station (e.g., a de-waxing station, a de-paraffinizing station, or the like), staining station, cover-slipping station, or the like. For example, the processing stations 404, 406, 408 can be a de-paraffinizing station, staining station, and cover-slipping station, respectively.

A transport device 418 transports specimen-bearing microscope slides between the drying station 402 and the other stations 404, 406, 408. The transport device 418 can include, without limitation, one or more elevators, slide handlers, slide trays, slide holders, or the like. Slide handlers can include, but are not limited to, slide manipulators, X-Y-Z transport systems, robotic systems, or other automated systems capable of receiving and transporting slides. A robotic system can include, without limitation, one or more pick and place robots, robotic arms, or the like.

Figure 12:
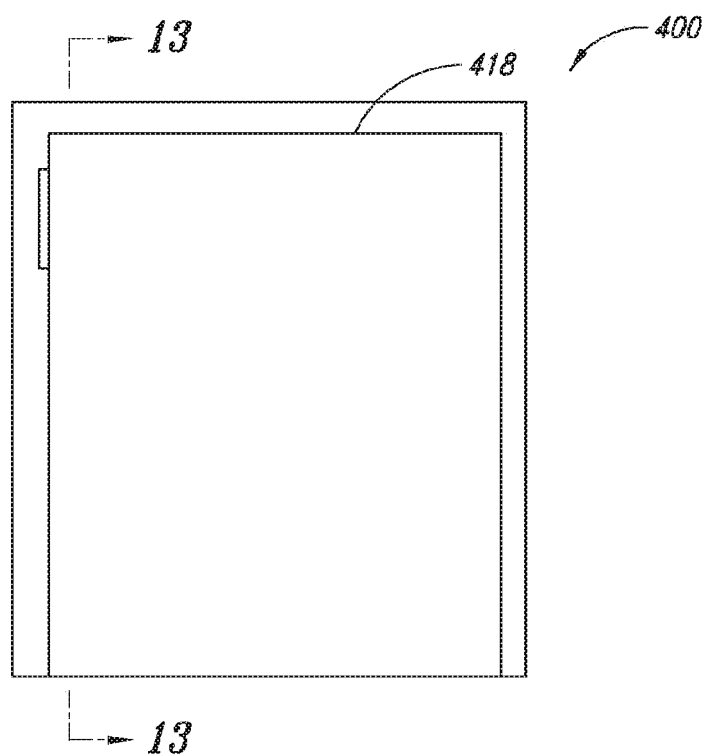
FIG. 12 is a side elevational view of the apparatus of FIG. 11.
Figure 13:
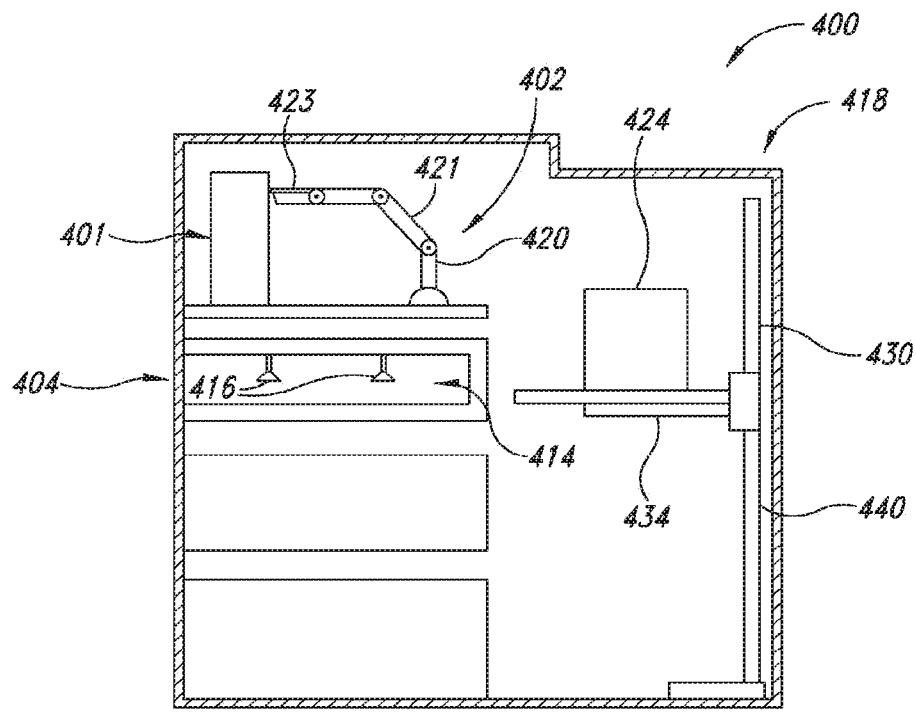
FIG. 13 is a cross-sectional view of the apparatus of FIG. 11 taken along a line 13-13 of FIG. 12.

Referring to FIGS. 11-13, the drying station 402 includes the slide dryer 401 and a slide handler 420, illustrated as a robotic slide handler. The slide dryer 401 generates heat for conductively heating the specimen-carrying microscope slides. The robotic slide handler 420 includes an arm 421 and an end effector 423 capable of picking up and carrying slides between the conductive slide heater 401 and a slide transporter 424, illustrated schematically in FIG. 13. The slide dryer 401 can be generally similar to the slide dryer 100 of FIGS. 1-3 or the slide dryer 300 of FIG. 10. Various types of other automated slide processing systems can also have the slide dryers and other features disclosed herein. For example, U.S. application Ser. No. 10/414,804 (U.S. Publication No. 2004/0002163) discloses various types of slide transporters, processing stations, and the like that can be used with or incorporated into the embodiments and features disclosed herein.

Wet microscope slides carrying freshly cut tissue specimens can be processed using the apparatus 400. An access door 430 can be opened, and a user can load specimen-bearing slides into the transport device 418. The transport device 418 can load the slides into the dryer station 402. After drying the specimen-bearing slides, the slides are sequentially delivered to the stations 404, 406, 408. The transport device 418 of FIG. 13 includes an elevator system 430 and a movable platform 434, shown carrying the slide transporter 424. The elevator system 430 moves the transporter 424 up and down a rail 440.

In some methods of using the apparatus 400, specimen-carrying microscope slides are loaded onto a slide tray, which is placed on the platform 434. The slide handler 420 loads the specimen-carrying microscope slides into the slide dryer 401. The slide dryer 401 dries the specimen-carrying microscope slides. After the specimen-carrying microscope slides are dried a sufficient amount, the slide handler 420 transports the slides back to the transporter 424.

The transporter 242 is vertically lowered and positioned adjacent to the processing station 404 for de-paraffinizing. The station 404 is capable of removing at least a portion of the embedding material of the specimen. The de-paraffinizing station 404 can be a bath-type, de-paraffinizing station or a spray-type, de-paraffinizing station. The illustrated de-paraffinizing station 404 includes a modular compartment 414 and includes one or more wash dispense nozzles 416 directed downwardly. De-paraffinizing substances are delivered onto the specimens using the nozzles 416. After removing the embedding material (e.g., paraffin), the slides can be rinsed with substances, such as de-ionized water, to remove the de-paraffinizing substance and the extra paraffin leaving the bare tissue sample adhered to the microscope slide.

Various de-paraffinizing substances may be used at the station 404. For example, the de-paraffinizing substances can be fluids, for example, aqueous-based fluids that promote separation of paraffin and tissue specimens, such as those disclosed in U.S. Pat. No. 6,855,559, issued Feb. 15, 2005 and U.S. Pat. No. 6,544,798, issued Apr. 8, 2003, including de-ionized water, citrate buffer (pH 6.0-8.0), tris-HCl buffer (pH 6-10), phosphate buffer (pH 6.0-8.0), acidic buffers or solutions (pH 1-6.9), basic buffers or solutions (pH 7.1-14), or the like. The substance may also contain one or more ionic or non-ionic surfactants. The de-paraffinizing substances can be heated. For example, the substances (e.g., fluids) may be heated to a temperature greater than the melting point of the embedding material, e.g., between 60-70 degrees Celsius. U.S. Pat. No. 7,303,725, issued Dec. 4, 2007, discloses various components (e.g., probes, filters, sprayers, etc.) for use with de-paraffinizing substances.

In some embodiments, the station 404 also includes one or more heating elements for baking the embedding material. The slides can be heated to soften the embedding material to facilitate material removal.

After the station 404 has processed the specimen-carrying slides, the transport system 424 delivers the specimen-carrying slides to the station 406 for staining. A desired stain is applied to the tissue samples. The stain can be a biological or chemical substance which, when applied to targeted molecules in tissue, renders the tissue detectable under an instrument. Stains include, without limitation, detectable nucleic acid probes, antibodies, hematoxylin, eosin, and dyes (e.g., iodine, methylene blue, Wright's stain, etc.).

After the specimens are stained, the specimen-bearing slides are transported to the cover-slipping station 408. In other embodiments, the station 408 is a drying station. The station 408 dries the stained slides and the slides are ready for cover slipping. In some embodiments, the drying station 408 conductively heats the stained specimens using a slide dryer, such as those discussed in connection with FIGS. 1-10. In other embodiments, the drying station 408 is in the form of a convection oven or microwave oven.

The apparatus 400 can also include other types of processing stations. The number, configurations, and types of processing stations can be selected based on the types of processing to be performed. For example, U.S. Pat. No. 7,396,508 discloses apparatuses for staining and treating tissues. U.S. Pat. No. 7,396,508 is incorporated herein by reference in its entirety. In some embodiments, the processing station 406 includes a carousel type system, such as the carousel system disclosed in U.S. Pat. No. 7,396,508.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I claim:

1. An apparatus for automatically processing microscope slides carrying specimens, the apparatus comprising:
    a drying station including a slide dryer, wherein the drying station is configured to automatically hold the microscope slides at an angle of inclination to promote draining of liquid from the microscope slides, and wherein the slide dryer heats the microscope slides held at the angle of inclination such that a temperature along each of the microscope slides is higher than about 50 degrees Celsius to at least partially dry the specimens carried by the microscope slides;
    a staining station that automatically delivers stains onto the microscope slides to stain the at least partially dried specimens;
    a cover-slipping station that automatically places coverslips on the microscope slides;
    a transport device that automatically transports the microscope slides between the drying station, the staining station, and the cover-slipping station; and
    at least one controller programmed to
        command the transport device to transport the microscope slides, which carry transfer liquid and the specimens, to the drying station,
        command the drying station to position the microscope slides at the angle of inclination to drain the transfer liquid from the microscope slides, and
        command the transport device to transport the microscope slides that have been dried in the drying station to the staining station.

2. The apparatus of claim 1, wherein the drying station comprises a slide handler configured to automatically position the microscope slides at the angle of inclination.

3. The apparatus of claim 2, wherein the slide handler comprises at least one of a slide manipulator, an X-Y-Z transport system, a robotic arm, or a pick and place robot.

4. The apparatus of claim 1, wherein the angle of inclination is greater than about 75 degrees.

5. The apparatus of claim 1, wherein the drying station is configured to hold the microscope slides at the angle of inclination in a predetermined spaced apart arrangement.

6. The apparatus of claim 1, wherein the transport device is configured to (1) transport the microscope slides from the drying station to the staining station after the specimens are at least partially dried, and (2) transport the microscope slides from the staining station to the cover-slipping station after the specimens are stained.

7. The apparatus of claim 1, wherein the transport device is configured to vertically move the microscope slides between the drying station, the staining station, and the cover-slipping station.

8. The apparatus of claim 1, wherein the transport device comprises a slide tray that carries the microscope slides.

9. An apparatus for automatically processing microscope slides carrying specimens, the apparatus comprising:
  a drying station that automatically (1) holds the microscope slides at a substantially vertical orientation, and (2) heats the microscope slides held at the substantially vertical orientation to a temperature higher than about 50 degrees Celsius;
  a processing station configured to automatically dispense one or more fluids to contact the specimens carried by the microscope slides;
  a transport device configured to automatically transport the microscope slides between the drying station and the processing station; and
  a controller programmed to
    cause the transport device to transport the microscope slides carrying transfer liquid and the specimens to the drying station, and
    cause the drying station to position the microscope slides at the substantially vertical orientation to promote draining of the transfer liquid from the microscope slides.

10. The apparatus of claim 9, wherein the drying station comprises a slide handler that automatically positions the microscope slides at the substantially vertical orientation.

11. The apparatus of claim 9, wherein the substantially vertical orientation comprises an angle of inclination greater than about 75 degrees.

12. The apparatus of claim 9, wherein the drying station is configured to heat the microscope slide by convection.

13. The apparatus of claim 12, wherein the drying station comprises a convection oven.

14. The apparatus of claim 9, wherein the one or more fluids comprise a stain.

15. An apparatus for processing microscope slides carrying specimens, the apparatus comprising:
  a drying station that robotically positions the microscope slides at an inclined position, wherein the drying station automatically heats the microscope slides held at the inclined position such that a temperature along each of the microscope slides is higher than about 50 degrees Celsius to at least partially dry the specimens carried by the microscope slides;
  a staining station configured to automatically stain the at least partially dried specimens;
  a transport device configured to robotically transport the microscope slides between the drying station and the staining station; and
  one or more controllers programmed to
    command the transport device to move the microscope slides carrying transfer liquid and the specimens to the drying station, and
    command the drying station to position the microscope slides at the inclined position to promote draining of the transfer liquid from the microscope slides.

16. The apparatus of claim 15, wherein the drying station comprises a slide handler configured to robotically position the microscope slides at the inclined position.

17. The apparatus of claim 15, wherein the microscope slides at the inclined position are held at an angle of inclination greater than about 75 degrees.

18. The apparatus of claim 15, wherein the drying station comprises a conduction slide dryer or a convection oven.

19. The apparatus of claim 15, wherein the transport device comprises a slide tray that carries the microscope slides.

20. The apparatus of claim 19, wherein the microscope slides are carried by the slide tray during transportation of the microscope slides between the drying station and the staining station.

* * * * *